US012758530B2

(12) United States Patent
Makino et al.

(10) Patent No.: US 12,758,530 B2
(45) **Date of Patent: *Oct. 13, 2026**

(54) ANTIOXIDANT AND USE THEREOF

(71) Applicant: Bioradical Research Institute Corp., Yokohama (JP)

(72) Inventors: Keisuke Makino, Kyoto (JP); Toshiyuki Arai, Kyoto (JP); Yoko Arai, Kyoto (JP); Masaichi Lee, Kawasaki (JP)

(73) Assignee: Bioradical Research Institute Corp., Yokohama (JP)

(*) Notice: Subject to any disclaimer, the term of this patent is extended or adjusted under 35 U.S.C. 154(b) by 1093 days.

This patent is subject to a terminal disclaimer.

(21) Appl. No.: 17/424,334

(22) PCT Filed: Dec. 18, 2019

(86) PCT No.: PCT/JP2019/049670

§ 371 (c)(1),
(2) Date: Dec. 17, 2021

(87) PCT Pub. No.: WO2020/158225

PCT Pub. Date: Aug. 6, 2020

(65) Prior Publication Data

US 2022/0110916 A1 Apr. 14, 2022

(30) Foreign Application Priority Data

Jan. 28, 2019 (JP) ................................ 2019-011929

(51) Int. Cl.
*A61K 31/4155* (2006.01)
*A61P 39/06* (2006.01)

(52) U.S. Cl.
CPC .......... *A61K 31/4155* (2013.01); *A61P 39/06* (2018.01)

(58) Field of Classification Search
CPC ............................ A61K 31/4155; A61P 39/06
See application file for complete search history.

(56) References Cited

U.S. PATENT DOCUMENTS

| | | | | |
|---|---|---|---|---|
| 5,314,998 | A | 5/1994 | Smith et al. | |
| 6,312,478 | B1 * | 11/2001 | Goettel et al. | .......... D06P 5/138 548/366.1 |
| 6,399,767 | B1 | 6/2002 | Horne et al. | |
| 7,060,822 | B1 | 6/2006 | Arnold et al. | |
| 2007/0123577 | A1 | 5/2007 | Miyata et al. | |
| 2010/0016396 | A1 | 1/2010 | Imoto | |
| 2012/0035187 | A1 | 2/2012 | Ohta et al. | |
| 2016/0122341 | A1 | 5/2016 | Vakalopoulos et al. | |
| 2017/0291889 | A1 | 10/2017 | Barden et al. | |
| 2017/0313700 | A1 | 11/2017 | Vakalopoulos et al. | |
| 2018/0147875 | A1 | 5/2018 | Santo et al. | |

FOREIGN PATENT DOCUMENTS

| | | | | |
|---|---|---|---|---|
| CA | 2103972 | A1 | 3/1994 | |
| JP | S63-2045 | A | 1/1988 | |
| JP | H04-131842 | A | 5/1992 | |
| JP | H05-45787 | A | 2/1993 | |
| JP | H06-179828 | A | 6/1994 | |
| JP | H10-305665 | A | 11/1998 | |
| JP | 2000-514463 | A | 10/2000 | |
| JP | 2001-524987 | A | 12/2001 | |
| JP | 2006-008618 | A | 1/2006 | |
| JP | 2016-522214 | A | 7/2016 | |
| JP | 2017-528494 | A | 9/2017 | |
| JP | 2017-537922 | A | 12/2017 | |
| JP | 2018-089960 | A | 6/2018 | |
| WO | 2005/054205 | A1 | 6/2005 | |
| WO | 2008/093639 | A1 | 8/2008 | |
| WO | 2010/087313 | A1 | 8/2010 | |
| WO | 2010/087315 | A1 | 8/2010 | |
| WO | WO-2010087306 | A1 * | 8/2010 | ............. A61P 11/00 |

OTHER PUBLICATIONS

Hall, Adrian, et al. "Novel Methylene-Linked Heterocyclic EP1 Receptor Antagonists." Bioorganic & Medicinal Chemistry Letters, vol. 18, No. 5, Mar. 2008, pp. 1592-1597, doi:10.1016/j.bmcl.2008.01.071. (Year: 2008).*

Yang, Xiaohui, et al. "Synthesis and Antioxidant Activities of Novel 4,4'-arylmethylene-bis(1h-pyrazole-5-ol)s from Lignin." Chinese Journal of Chemistry, vol. 30, No. 3, Mar. 2012, pp. 670-674, doi:10.1002/cjoc.201280009. (Year: 2012).*

Finar and Godfrey, Journal of the Chemical Society (1954) 2293-8 CODEN: JCSOA9; ISSN: 0368-1769 (Year: 1954).*

Patani and LaVoie, Chemical Reviews, 1996, vol. 96, No. 8 (Year: 1996).*

Attaryan et al. ISSN 1070-3632, Russian Journal of General Chemistry, 2007, vol. 77, No. 6, pp. 1139-1140 (Year: 2007).*

Tian et al. Dalton Trans., 2014, 43, 8405 (Year: 2014).*

(Continued)

*Primary Examiner* — Sarah Pihonak
*Assistant Examiner* — Donna M Nestor
(74) *Attorney, Agent, or Firm* — Morgan, Lewis & Bockius LLP

(57) ABSTRACT

The present invention provides a new antioxidant. An antioxidant of the present invention includes:

a compound represented by the following formula (1) or a salt thereof:

(1)

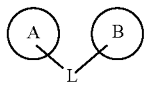

where in the formula (1), an A ring and a B ring may be the same or different and are a pyrazole ring having a substituent or a pyrazoline ring having a substituent, and L is a saturated or unsaturated hydrocarbon group.

17 Claims, 12 Drawing Sheets

(56) References Cited

OTHER PUBLICATIONS

Decision of Refusal issued in corresponding Japanese Patent Application No. 2020-569437 dated Jan. 10, 2023.
Khairnar et al., "Organophosphane-Catalyzed Direct Beta-Acylation of 4-Arylidene Pyrazolones and 5-Arylidene Thiazolones with Acyl Chlorides," Organic Letters, 22: 6868-6872 (2020).
Khairnar et al., "Diversity-Oriented Synthesis of Spiropentadiene Pyrazolones and 1H-Xoepino[2,3-c]pyrazoles from Doubly Conjugated Pyrazolones via Intramolecular Wittig Reaction," Organic Letters, 22 (12): 4760-4765 (2020).
Dirat et al., "Regioselective synthesis of 4-(2-alkyl-5-methyl-2H-pyrazol-3-yl)-piperidines," Tetrahedron Letters, 47: 1729-1731 (2006).
Sommani et al., "Effects of Edaravone on Singlet Oxygen Released from Activated Human Neutrophils," Journal of Pharmacological Society, 103: 117-120 (2007).
Knox et al., "Discovery and Clinical Evaluation of MK-8150, A Novel Nitric Oxide Donor With a Unique Mechanism of Nitric Oxide Release," Journal of the American Heart Association, e003493 (2016).
Lesnov et al., "Di-(1-hexyl-5-hydroxy-3-methyl-4-pyrazolyl)methane as an Extraction Reagent for Metal Ions," (see English abstract and ISR).
Pavolov et al., "Biological activity of some pyrazolone derivatives," Pharmaceutical Chemistry Journal, 32: 370-372 (1998) (see ISR).
International Search Report (ISR) issued in corresponding International Patent Application No. PCT/JP2019/049670 dated Feb. 4, 2020.
Notice of Payment of Restoration Fee for Unity issued in Chinese Patent Application No. 202180059651.6, dated Mar. 8, 2025.
Office Action issued in related U.S. Appl. No. 17/783,104, dated Apr. 22, 2025.
Office Action issued in the corresponding JP Patent Application No. 2024-073944, issued Aug. 5, 2025.
Parker, S. J., & Watkins, P. E. (2001). Experimental models of gram-negative sepsis. British journal of surgery, 88(1), 22-30, https://doi.org/10.1046/j.1365-2168.2001.01632.x.
Gorabi, A. M., Kiaie, N., Khosrojerdi, A., Jamialahmadi, T., Al-Rasadi, K., Johnston, T. P., & Sahebkar, A. (2022). Implications for the role of lipopolysaccharide in the development of atherosclerosis. Trends in cardiovascular medicine, 32(8), 525-533, https://doi.org/10.1016/j.tcm.2021.08.015.—abstract.
Ahmed, S. H., He, Y. Y., Nassief, A., Xu, J., Xu, X. M., & Hsu, C. Y. (2000). Effects of lipopolysaccharide priming on acute ischemic brain injury. Stroke, 31(1), 193-199, https://doi.org/10.1161/01.STR.31.1.193.
Chen, H., Bai, C., & Wang, X. (2010). The value of the lipopolysaccharide-induced acute lung injury model in respiratory medicine. Expert review of respiratory medicine, 4(6), 773-783, https://doi.org/10.1586/ers.10.71—abstract.
Nazem, A., Sankowski, R., Bacher, M., & Al-Abed, Y. (2015). Rodent models of neuroinflammation for Alzheimer's disease. Journal of neuroinflammation, 12(1), 74, https://doi.org/10.1186/s12974-015-0291-y.
Doi, K., Leelahavanichkul, A., Yuen, P. S., & Star, R. A. (2009). Animal models of sepsis and sepsis-induced kidney injury. The Journal of clinical investigation, 119(10), 2868-2878, https://doi.org/10.1172/JCI39421.
Southey, A., Tanaka, S., Murakami, T., Miyoshi, H., Ishizuka, T., Sugiura, M., . . . & Sugita, T. (1998). Pathophysiological role of nitric oxide in rat experimental colitis. International journal of immunopharmacology, 19(11-12), 669-676, https://doi.org/10.1016/S0192-0561(97)00107-0.
Dumitrescu, A. L., Abd El-Aleem, S., Morales-Aza, B., & Donaldson, L. F. (2004). A model of periodontitis in the rat: effect of lipopolysaccharide on bone resorption, osteoclast activity, and local peptidergic innervation. Journal of Clinical Periodontology, 31(8), 596-603, https://doi.org/10.1111/j.1600-051X.2004.00528.x.
Ismail et al., "Carotid Artery Stenosis: A Look Into the Diagnostic and Management Strategies, and Related Complications", Cureus, vol. 15 No. 5, 2023, pp. 1-16.
Premer et al., "Rethinking Endothelial Dysfunction as a Crucial Target in Fighting Heart Failure", Mayo Clin Proc Inn Qual Out, vol. 3, No. 1, 2019, pp. 1-13.
Rajendran et al., "The Vascular Endothelium and Human Diseases", International Journal of Biological Sciences, vol. 9, No. 10, 2013, pp. 1057-1069.
Silva et al., "The "Silent Enemy" Called Renal Artery Stenosis: A Mini-Review", Journal of Vascular Diseases, vol. 4, No. 10, 2025, pp. 1-26.
Sun et al., "Role of Endothelial Dysfunction in Cardiovascular Diseases: The Link Between Inflammation and Hydrogen Sulfide", Frontiers in Pharmacology, vol. 10, Article 1568, Jan. 2020, pp. 1-15.
Wijeratne et al., "Carotid artery stenosis and inflammatory biomarkers: the role of inflammation-induced immunological responses affecting the vascular systems", Annals of Translational Medicine, vol. 8, No. 19, 2020, pp. 1-9.
Office Action issued in Japanese Patent Application No. 2022-539533, dated Nov. 11, 2025.

* cited by examiner 0 min 30 min 60 min 90 min 120 min 150 min 180 min 0 min 20 min 30 min 50 min 60 min 180 min 90 min

ANTIOXIDANT AND USE THEREOF

TECHNICAL FIELD

The present invention relates to an antioxidant and use thereof.

BACKGROUND ART

Reactive oxygen species are generated by oxygen metabolism that is essential for life activity. In addition, reactive oxygen species have been reported to be involved in various diseases because they induce tissue and cell disorders when they are excessively generated due to their high reactivity. Thus, reactive oxygen species eliminators have been developed. However, many reactive oxygen species eliminators are unstable. Therefore, only edaravone (5-methyl-2-phenyl-2, 4-dihydro-3H-pyrazol-3-one, trade name: "Radicut," produced by Mitsubishi Tanabe Pharma Corporation) is a practical reactive oxygen species eliminator used clinically (Non-Patent Literature 1).

CITATION LIST

Non-Patent Literature

Non-Patent Literature 1: Piyanart Sommani et al., "Effects of edaravone on Singlet Oxygen Released From Activated Human Neutrophils," J. Pharmacol. Sci., 2007, vol. 103, pages 117-120.

SUMMARY OF INVENTION

Technical Problem

Edaravone is an antioxidant that functions to scavenge radicals generated at the time of restarting blood flow after an acute cerebral ischemic attack or cerebral infarction, in particular singlet oxygen, to protect cranial nerves, and is a potent radical scavenger. However, edaravone is unstable in an aqueous solution and easily oxidized so that it needs to be stored in a reducing aqueous solution.

With the foregoing in mind, it is an object of the present invention to provide a new antioxidant.

Solution to Problem

In order to achieve the above object, the present invention provides an antioxidant including:

a compound represented by the following formula (1) or a salt thereof:

(1)

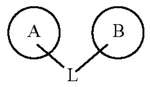

where in the formula (1), an A ring and a B ring may be the same or different and are a pyrazole ring having a substituent or a pyrazoline ring having a substituent, and L is a saturated or unsaturated hydrocarbon group.

The present invention also provides a cytoprotective agent (hereinafter, also referred to as a protective agent) including: the antioxidant according to the present invention.

The present invention also provides a pharmaceutical for a disease caused by oxidative stress (hereinafter, also referred to as a pharmaceutical), including: the antioxidant according to the present invention.

The present invention also provides an antioxidation method using the antioxidant according to the present invention.

The present invention also provides a pyrazole ring derivative or a salt thereof represented by the following formula (4):

(4)

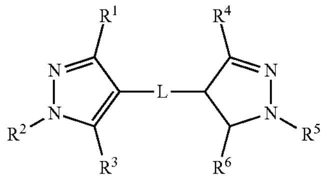

where in the formula (4), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is an alkyl group having 2 or more carbon atoms, $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is an alkyl group having 2 or more carbon atoms, $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, L is a saturated or unsaturated hydrocarbon group.

The present invention also provides a cell protection method using the cytoprotective agent according to the present invention.

Advantageous Effects of Invention

According to the present invention, by including the compound represented by the formula (1) or a salt thereof, reactive oxygen species can be scavenged.

BRIEF DESCRIPTION OF DRAWINGS

In FIG. 10, (A) shows the result of a thin blood vessel, (B) shows the result of a medium blood vessel, and (C) shows the result of a thick blood vessel.

DESCRIPTION OF EMBODIMENTS

Figure 1A:
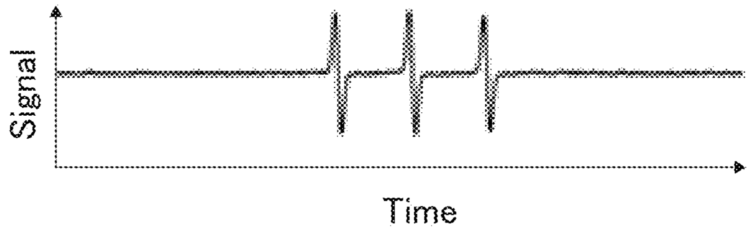
FIG. 1 shows graphs showing ESR results in Example 3.

As described above, the antioxidant of the present invention includes:

a compound represented by the following formula (1) or a salt thereof:

(1)

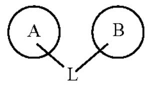

where in the formula (1), an A ring and a B ring may be the same or different and are a pyrazole ring having a substituent or a pyrazoline ring having a substituent, and L is a saturated or unsaturated hydrocarbon group.

The antioxidant of the present invention is characterized in that it includes a compound represented by the formula (1) or a salt thereof, and other configurations and conditions are not particularly limited. It is presumed that the antioxidant of the present invention scavenges reactive oxygen species by the following mechanism. Note that the present invention is not limited in any way to the following presumption. In a compound represented by the formula (1) or a salt thereof, it is presumed that a pyrazole ring or a pyrazoline ring linked by a functional group L alone or together with a functional group L forms a conjugated system. It is also presumed that, since the stability of the compound is high due to the conjugated system formed, the compound of the formula (1) can absorb the radical or energy possessed by the reactive oxygen species and functions as an antioxidant.

In the present invention, the "antioxidant" means, for example, an agent that scavenges reactive oxygen species. Examples of the reactive oxygen species include radical species such as hydroxyl radical (•OH), alkoxy radical (LO•), peroxy radical (LOO•), hydroperoxy radical (HOO•), nitrogen monoxide (NO•), nitrogen dioxide ($NO_2$•), superoxide anion ($O_2^-$), and the like; and non-radical species such as singlet oxygen ($^1O_2$), ozone ($O_3$), hydrogen peroxide ($H_2O_2$), and the like. The antioxidant of the present invention may scavenge, for example, any one of or two or more of the reactive oxygen species, and it is preferable to scavenge singlet oxygen ($^1O_2$). The scavenging of the reactive oxygen species can also be referred to as, for example, elimination of reactive oxygen species. The scavenging of the reactive oxygen species is carried out, for example, by the antioxidant of the present invention donating a hydrogen atom to the reactive oxygen species and converting the reactive oxygen species into other molecules (e.g., water) which are more stable. The antioxidant of the present invention may also be referred to as, for example, a scavenger of reactive oxygen species, radical species, or singlet oxygen, or an eliminator of reactive oxygen species, radical species, or singlet oxygen. In addition, the antioxidant of the present invention can suppress or prevent oxidation by reactive oxygen species of other molecules coexisting, for example. Thus, the antioxidant of the present invention can also be referred to as an oxidation inhibitor or an oxidation depressant, for example.

The reactive oxygen species scavenging ability can be evaluated, for example, by a reactive oxygen evaluation method using 2, 2, 6, 6-tetramethyl-4-piperidone (TMPD). When the reactive oxygen species is singlet oxygen, the singlet oxygen-scavenging ability can be measured according to Example 3 described below.

Each substituent in the compound represented by the formula (1) will be described below with reference to examples. Regarding the description of each substituent, reference can be made to specific examples in the description of other substituents, unless otherwise stated. In addition, when there is no particular reference in the following description, the description of the compound represented by the formula (1) can be applied to the description of the salt of the compound represented by the formula (1), for example.

When the compound represented by the formula (1) has an asymmetric carbon atom, the compound represented by the formula (1) may be present as, for example, a racemate, an enantiomer of R and S thereof, or a mixture of R and S in any proportion. The compound represented by the formula (1) may have two or more asymmetric centers. In this case, the compound represented by the formula (1) may contain a diastereomer and a mixture thereof. When the compound represented by the formula (1) has a double bond in a molecule, the compound of the present invention may include, for example, a form of a geometric isomer of cis and trans isomers.

In the formula (1), the A ring and the B ring may be the same or different and are each a pyrazole ring having a substituent or a pyrazoline ring having a substituent. The pyrazole ring having a substituent may be, for example, a pyrazole ring represented by the following formula (2). Further, the pyrazoline ring having a substituent may be, for example, a pyrazoline ring represented by the following formula (3)

(2)

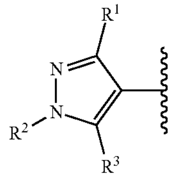

-continued (3)

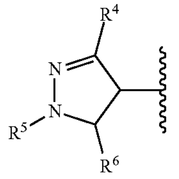

In the formula (2), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably a hydrogen atom, a halogen atom, or an alkyl group.

Examples of the halogen atom include a fluorine atom, a chlorine atom, a bromine atom, and an iodine atom.

Examples of the alkyl group include linear, branched, or cyclic saturated or unsaturated alkyl groups having 1 to 20 or 1 to 10 carbon atoms. Specific examples of the alkyl group include a methyl group, an ethyl group, an n-propyl group, an i-propyl group, an n-butyl group, an i-butyl group, a t-butyl group, an n-pentyl group, an i-pentyl group, a t-pentyl group, an n-hexyl group, an i-hexyl group, a t-hexyl group, an n-heptyl group, an i-heptyl group, a t-heptyl group, an n-octyl group, an i-octyl group, a t-octyl group, an n-nonyl group, an i-nonyl group, a t-nonyl group, an n-decyl group, an i-decyl group, a t-decyl group, an n-undecyl group, an i-undecyl group, an n-dodecyl group, an i-dodecyl group, an n-tridecyl group, an i-tridecyl group, an n-tetradecyl group, an i-tetradecyl group, an n-pentadecyl group, an i-pentadecyl group, an n-hexadecyl group, an i-hexadecyl group, an n-heptadecyl group, an i-heptadecyl group, an n-octadecyl group, an i-octadecyl group, an n-nonadecyl group, and an i-nonadecyl group. The alkyl group is preferably, for example, a linear saturated alkyl group having 1 to 6 carbon atoms, and more preferably a methyl group or an ethyl group.

In the alkoxy group (RO—), R is an alkyl group, and reference can be made to the description of the alkyl group described above.

In the hydroxyalkyl group (HOR—), R is an alkyl group, and reference can be made to the description of the alkyl group described above.

In the acyl group (RCO—), R is an alkyl group, and reference can be made to the description of the alkyl group described above.

Examples of the alkenyl group include those having one or more double bonds in the alkyl group. Examples of the alkenyl group include alkenyl groups having 2 to 20 carbon atoms, preferably 2 to 6 carbon atoms, and specific examples thereof include a vinyl group, an allyl group, a 1-propenyl group, a 2-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, and a 2-methyl-2-butenyl group.

Examples of the alkynyl group include those having one or more triple bonds in the alkyl group. Examples of the alkynyl group include alkynyl groups having 2 to 20 carbon atoms, preferably 2 to 6 carbon atoms, and specific examples thereof include an ethynyl group, a 1-propynyl group, a 2-propynyl group, a 1-butynyl group, a 2-butynyl group, a 3-butynyl group, a 1-methyl-2-propynyl group, a 1-pentinyl group, a 2-pentinyl group, a 3-pentinyl group, a 4-pentinyl group, and a 1-methyl-3-butynyl group. The alkynyl group may further have, for example, one or more double bonds.

The aryl group that may have a substituent may be an aryl group, or the aryl group may be substituted with a substituent. The aryl group that may have a substituent is, for example, an aryl group having 6 to 20 total carbon atoms, including the number of carbon atoms in the substituent, and specific examples thereof include a phenyl group, a tolyl group, a xylyl group, an alkyloxyphenyl group (e.g., a methoxyphenyl group, an ethoxyphenyl group, etc.), a hydroxyphenyl group, a halogenophenyl group (e.g., a fluorophenyl group, a chlorophenyl group, a bromophenyl group, etc.), an alkylphenyl group (e.g., a methylphenyl group, an ethylphenyl group, a propylphenyl group, etc.), a cyanophenyl group, a propyloxyphenyl group, and a 4-sulfophenyl group, and a phenyl group or a 4-sulfophenyl group is preferable.

In the formula (2), $R^2$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and is preferably an alkyl group or an aryl group that may have a substituent. The alkyl group is preferably a linear saturated alkyl group having 1 to 6 carbon atoms, and more preferably a methyl group or an ethyl group. As the aryl group that may have a substituent, a phenyl group or a 4-sulfophenyl group is preferable.

In the formula (2), $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and is preferably a hydrogen atom, a halogen atom, or a hydroxy group. The alkyl group is preferably a linear saturated alkyl group having 1 to 6 carbon atoms, and more preferably a methyl group or an ethyl group.

In the formula (3), $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably a hydrogen atom, a halogen atom, or an alkyl group. The alkyl group is preferably a linear saturated alkyl group having 1 to 6 carbon atoms, and more preferably a methyl group or an ethyl group.

In the formula (3), $R^5$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably an alkyl group or an aryl group that may have a substituent. The alkyl group is preferably a linear saturated alkyl group having 1 to 6 carbon atoms, and more preferably a methyl group or an ethyl group. As the aryl group that may have a substituent, a phenyl group or a 4-sulfophenyl group is preferable.

In the formula (3), $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably a hydrogen atom, an oxygen atom, a halogen atom, or a hydroxy group.

In the formula (1), L is a saturated or unsaturated hydrocarbon group. Examples of L include saturated hydrocarbon groups such as an alkyl group and the like; and unsaturated hydrocarbon groups such as an alkenyl group, an alkynyl group, and the like. Regarding the alkyl group, reference can be made to the description as to the alkyl group in $R^1$. The number of carbon atoms of the main chain in L is preferably an odd number, and as a specific example, the number of carbon atoms is preferably 1, 3, 5, or 7, more preferably 1, 3 or 5, and still more preferably 3.

Examples of the alkenyl group include those having one or more double bonds in the alkyl group. Examples of the alkenyl group include alkenyl groups having 2 to 20 carbon atoms, preferably 2 to 6 carbon atoms, and specific examples thereof include a vinyl group, an allyl group, a 1-propenyl group, a 2-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, and a 2-methyl-2-butenyl group.

Examples of the alkynyl group include those having one or more triple bonds in the alkyl group. Examples of the alkynyl group include alkynyl groups having 2 to 20 carbon atoms, preferably 2 to 6 carbon atoms, and specific examples thereof include an ethynyl group, a 1-propynyl group, a 2-propynyl group, a 1-butynyl group, a 2-butynyl group, a 3-butynyl group, a 1-methyl-2-propynyl group, 1-pentinyl group, 2-pentinyl group, 3-pentinyl group, 4-pentinyl group, and 1-methyl-3-butynyl group. The alkynyl group may further have, for example, one or more double bonds.

L is preferably an unsaturated hydrocarbon group having 1 to 6 carbon atoms, more preferably an alkenyl group having 2 to 6 carbon atoms, and specific examples thereof include a 1-propenyl group and a 2-propenyl group.

The compound represented by the formula (1) preferably includes a compound represented by the following formula (4):

(4)

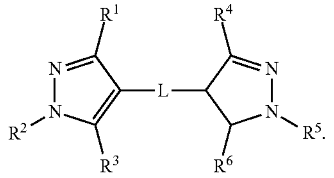

In the formula (4),
- $R^1$ is a hydrogen atom, a halogen atom, or an alkyl group,
- $R^2$ is an alkyl group or an aryl group that may have a substituent,
- $R^3$ is a hydrogen atom, a halogen atom, or a hydroxy group,
- $R^4$ is a hydrogen atom, a halogen atom, or an alkyl group,
- $R^5$ is an alkyl group or an aryl group that may have a substituent,
- $R^6$ is a hydrogen atom, an oxygen atom, a halogen atom, or a hydroxy group, and
- L is a saturated or unsaturated hydrocarbon group having 1 to 6 carbon atoms.

In the formula (4),
- $R^1$ is a hydrogen atom or an alkyl group,
- $R^2$ is an alkyl group or an aryl group that may have a substituent,
- $R^3$ is a hydroxy group,
- $R^4$ is a hydrogen atom or an alkyl group,
- $R^5$ is an alkyl group or an aryl group that may have a substituent,
- $R^6$ is an oxygen atom or a hydroxy group, and
- L is preferably an unsaturated hydrocarbon group having 1 to 6 carbon atoms, and more preferably an unsaturated hydrocarbon group having 1, 3, or 5 carbon atoms.

As a specific example, the compound represented by the formula (1) preferably includes a compound represented by the following formula (5), because, for example, it can suppress the decomposition reaction in an aqueous solution or an aqueous solvent such as a phosphate buffer, it can scavenge the superoxide and the singlet oxygen, it has no or low cytotoxicity, and it can suppress the generation of a byproduct having cytotoxicity even after the reaction with singlet oxygen. The compound of the following formula (5) may also be referred to as, for example, 2,4-dihydro-4-[3-(1-ethyl-5-hydroxy-3-methyl-1H-pyrazol-4-yl)-2-propen-1-ylidene]-2-ethyl-5-methyl-3H-pyrazol-3-one. Hereinafter, the compound of the following formula (5) is also referred to as BisEp-C3.

(5)

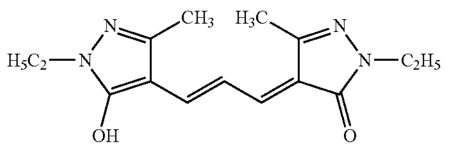

The compound represented by the formula (1) preferably includes a compound represented by the following formula (6), because, for example, it can suppress the decomposition reaction in an aqueous solution or an aqueous solvent such as a phosphate buffer, it can scavenge the superoxide and the singlet oxygen, and it has no or low cytotoxicity. The compound of the following formula (6) may also be referred to as, for example, 2,4-dihydro-4-[3-(5-hydroxy-3-methyl-1-phenyl-1H-pyrazol-4-yl)-2-propen-1-ylidene]-5-methyl-2-phenyl-3H-pyrazol-3-one. The compound of the following formula (6) is, for example, a compound registered under the Cas Registration No.: 27981-68-6. Hereinafter, the compound of the following formula (6) is also referred to as ED2AP.

(6)

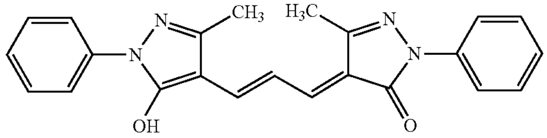

The compound represented by the formula (1) includes, for example, a compound represented by the following formula (7). The compound of the following formula (7) may also be referred to as, for example, 4-[4,5-dihydro-4-[3-[5-hydroxy-3-methyl-1-(4-sulfophenyl)-1H-pyrazol-4-yl]-2-propen-1-ylidene]-3-methyl-5-oxo-1H-pyrazol-1-yl]-benzenesulfonic acid. In the compound represented by the following formula (7), hydrogen in the sulfo group may be sodium. The sodium salt of the compound represented by the following formula (7) is, for example, a compound registered under the Cas Registration No.: 63870-34-8.

(7)

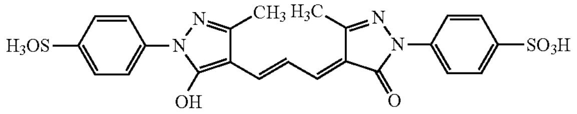

The compound represented by the formula (1) includes, for example, a compound represented by the following formula (8). The compound of the following formula (8) may also be referred to as, for example, 2,4-dihydro-4-[3-(5-hydroxy-1,3-dimethyl-1H-pyrazol-4-yl)-2-propen-1-ylidene]-2,5-dimethyl-3H-pyrazol-3-one. The compound represented by the following formula (8) is, for example, a compound registered under the Cas Registration No.: 242129-71-1.

(8)

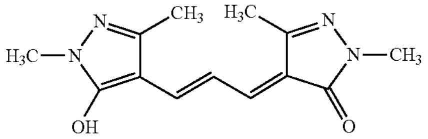

The compound represented by the formula (1) includes, for example, a compound represented by the following formula (9). The compound of the following formula (9) may also be referred to as, for example, 2,4-dihydro-4-[(5-hydroxy-1,3-dimethyl-1H-pyrazol-4-yl)methylene]-2,5-dimethyl-3H-pyrazol-3-one. Hereinafter, the compound of the following formula (9) is also referred to as BisEp-C1.

(9)

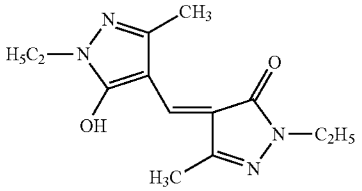

The compound represented by the formula (1) includes, for example, a compound represented by the following formula (10). The compound of the following formula (10) may also be referred to as, for example, Solvent Yellow 93 or 2,4-dihydro-4-[(5-hydroxy-3-methyl-1-phenyl-1H-pyrazol-4-yl)methylene]-5-methyl-2-phenyl-3H-pyrazol-3-one. The compound represented by the following formula (10) is, for example, a compound registered under the Cas Registration No.: 4174-09-8.

(10)

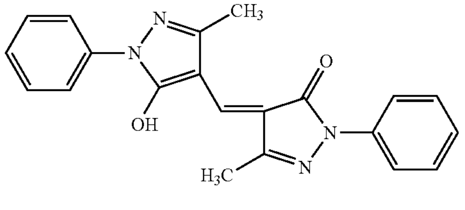

The compound represented by the formula (1) includes, for example, a compound represented by the following formula (11). The compound of the following formula (11) may also be referred to as, for example, 2,4-dihydro-4-[(5-hydroxy-1,3-dimethyl-1H-pyrazol-4-yl)methylene]-2,5-dimethyl-3H-pyrazol-3-one. The compound represented by the following formula (11) is, for example, a compound registered under the Cas Registration No.: 151589-04-7.

(11)

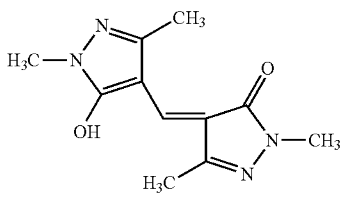

The compound represented by the formula (1) includes, for example, a compound represented by the following formula (12).

(12)

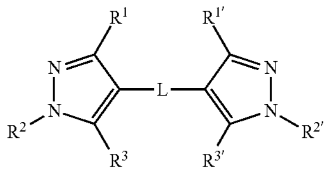

In the formula (12), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^{1'}$ is a hydrogen atom, a halogen atom, or an alkyl group, $R^{2'}$ is an alkyl group or an aryl group that may have a substituent, $R^{3'}$ is a hydrogen atom, a halogen atom, an alkyl group, or a hydroxy group, and L is a saturated or unsaturated hydrocarbon group having 1 to 6 carbon atoms.

In the formula (12), $R^1$ is a hydrogen atom or an alkyl group, $R^2$ is an alkyl group or an aryl group that may have a substituent, $R^3$ is a hydroxy group, $R^{1'}$ is a hydrogen atom or an alkyl group, $R^{2'}$ is an alkyl group or an aryl group that may have a substituent, $R^{3'}$ is an alkyl group or a hydroxy group, and L is preferably a saturated or unsaturated hydrocarbon group having 1 to 6 carbon atoms.

As a specific example, the compound represented by the formula (1) includes, for example, a compound represented by the following formula (13). The compound of the following formula (13) may also be referred to as, for example, 4,4'-methylenebis[1-ethyl-3-methyl-1H-pyrazol-5-ol]. The compound of the following formula (13) is also referred to as BisEp-C1 ($H_2$).

(13)

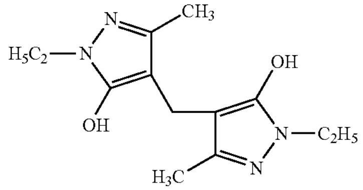

The compound represented by the formula (1) includes, for example, a compound represented by the following formula (14). The compound of the following formula (14) may also be referred to as, for example, 4,4'-methylenebis [3-methyl-1-phenyl-1H-pyrazol-5-ol]. The compound represented by the following formula (14) is, for example, a compound registered under the Cas Registration No.: 98395-58-5.

(14)

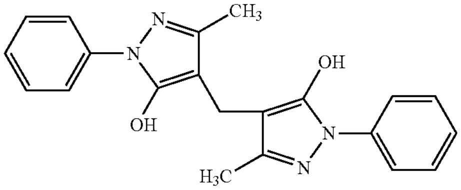

The compound represented by the formula (1) includes, for example, a compound represented by the following formula (15). The compound of the following formula (15) may also be referred to as, for example, 4,4'-methylenebis [1-hexyl-3-methyl-1H-pyrazol-5-ol]. The compound represented by the following formula (15) is, for example, a compound registered under the Cas Registration No.: 153231-80-2.

(15)

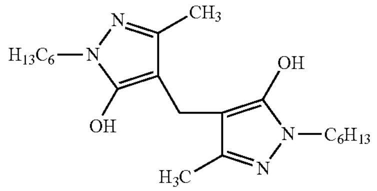

The compound represented by the formula (1) may be, for example, an isomer. The isomer may be, for example, a tautomer or a stereoisomer. The tautomer or stereoisomer may include, for example, all theoretically possible tautomers or stereoisomers. In addition, in the present invention, the configuration of each substituent is not particularly limited. In the antioxidant of the present invention, the compound represented by the formula (1) may be, for example, a hydrate of a compound represented by the formula (1) or a salt thereof, or a solvate.

In the present invention, the salt of the compound represented by the formula (1) is not particularly limited, and is, for example, a pharmaceutically acceptable salt. The pharmaceutically acceptable salt is not particularly limited, and examples thereof include alkali metal salts such as sodium salt, potassium salt, and the like; alkaline earth metal salts such as calcium salt, magnesium salt, and the like; ammonium salts; aliphatic amine salts such as trimethylamine salt, triethylamine salt, dichlorohexylamine salt, ethanolamine salt, diethanolamine salt, triethanolamine salt, brocaine salt, and the like; aralkylamine salts such as N,N-dibenzylethylenediamine, and the like; heterocyclic aromatic amine salts such as pyridine salt, picoline salt, quinoline salt, isoquinoline salt, and the like; quaternary ammonium salts such as tetramethylammonium salt, tetraethylammonium salt, benzyltrimethylammonium salt, benzyltributylammonium salt, methyltrioctylammonium salt, tetrabutylammonium salt, and the like; amino acid salts such as arginine salt, lysine salt, aspartate salt, glutamate salt, and the like; inorganic acid salts such as hydrochloride, sulfate, nitrate, phosphate, carbonate, bicarbonate, perchlorate, and the like; aliphatic organic acid salts or aromatic organic acid salts such as acetate, propionate, succinate, glycolate, lactate, maleate, fumarate, tartrate, malate, citrate, ascorbate, hydroxymaleate, pyruvate, phenyl acetate, benzoate, 4-aminobenzoate, anthranylate, 4-hydroxybenzoate, salicylate, 4-aminosalicylate, pamoate, gluconate, nicotinate, and the like; and sulfonates such as methane sulfonate, isethionate, ethane sulfonate, benzene sulfonate, halobenzene sulfonate, p-toluene sulfonate, toluene sulfonate, naphthalene sulfonate, sulfanilate, cyclohexyl sulfamate, and the like.

The antioxidant of the present invention may be used, for example, in vivo or in vitro. The antioxidant of the present invention may be composed of, for example, a plurality of components. In this case, the antioxidant of the present invention may also be referred to as an antioxidant composition, for example.

The subject of administration of the antioxidant of the present invention is not particularly limited. When the antioxidant of the present invention is used in vivo, examples of the subject of administration include humans and non-human animals excluding humans. Examples of the non-human animal include mice, rats, rabbits, dogs, sheep, horses, cats, goats, monkeys, and guinea pigs. When the antioxidant of the present invention is used in vitro, examples of the subject of administration include cells, tissues, and organs, and examples of the cells include cells collected from a living body and cultured cells.

The use condition (administration condition) of the antioxidant of the present invention is not particularly limited, and for example, an administration form, an administration period, a dosage, and the like can be appropriately determined depending on the type of the subject of administration, and the like.

The dosage of the antioxidant of the present invention is not particularly limited. When the antioxidant of the present invention is used in vivo, the dosage can be appropriately determined, for example, depending on the type, symptom, age, administration method, and the like of the subject of administration. As a specific example, when the antioxidant is administered to a human, the dosage of the compound represented by the formula (1) per day in total is, for example, 0.1 to 1000 mg, 1 to 1000 mg, 10 to 1000 mg, or 10 to 100 mg, and preferably 10 to 1000 mg, 30 to 1000 mg, 10 to 100 mg, or 30 to 100 mg. The number of administrations per day is, for example, 1 to 5 times, 1 to 3 times, or once or twice, and is preferably 1 to 3 times, or once or twice. In the antioxidant of the present invention, the content of the compound represented by the formula (1) is not particularly limited, and can be appropriately set according to, for example, the aforementioned dosage per day.

The administration form of the antioxidant of the present invention is not particularly limited. When the antioxidant of the present invention is administered in vivo, it may be administered orally or parenterally. Examples of the parenteral administration include intravenous injection (intravenous administration), intramuscular injection (intramuscular administration), transdermal administration, subcutaneous administration, intradermal administration, enteral administration, rectal administration, vaginal administration, nasal administration, pulmonary administration, intraperitoneal administration, and topical administration.

The dosage form of the antioxidant of the present invention is not particularly limited, and can be appropriately determined depending on, for example, the administration form. Examples of the dosage form include a liquid form and a solid form. Specific examples of the dosage form include preparations for oral administration such as controlled release formulations (enteric formulation, sustained release formulation, etc.), capsules, liquids and solutions for oral administration (elixir, suspension, emulsion, aromatic water, lemonade, etc.), syrups (preparation for syrup, etc.), granules (effervescent granule, fine granule, etc.), powders, tablets (orally disintegrating tablet/orodispersible tablet, chewable tablet, effervescent tablet, dispersible tablet, soluble tablet, coated tablet, etc.), pills, jellies for oral administration, and the like; preparations for oro-mucosal application such as tablets for oro-mucosal application (medicated chewing gum, sublingual tablet, troche/lozenge, drop, buccal tablet, mucoadhesive tablet, etc.), sprays for oro-mucosal application, semi-solid preparation for oro-mucosal application, preparation for gargles, and the like: preparations for injection such as injections (implant/pellet, prolonged release injection, parenteral infusion (preparation for infusion), lyophilized injection, powder for injection, prefilled syringe, cartridge, etc.); preparations for dialysis such as dialysis agents (peritoneal dialysis agent and hemodialysis agent), and the like; preparations for inhalation such as inhalations (metered-dose inhaler, inhalation solution, dry powder inhaler, etc.); preparations for ophthalmic application such as ophthalmic ointments, ophthalmic preparations, and the like; preparations for otic application such as ear preparations; preparations for nasal application such as nasal preparations (nasal solution, nasal dry powder inhalers, etc.) and the like; preparations for rectal application such as suppositories for rectal application, semi-solid preparations for rectal application, enemas for rectal application, and the like; preparations for vaginal application such as suppositories for vaginal use, tablets for vaginal use, and the like; and preparations for cutaneous application such as liquids and solutions for cutaneous application (spirit, liniment, lotion, etc.), creams, gels, solid dosage forms for cutaneous application (powder for cutaneous application, etc.), sprays for cutaneous application (aerosol for cutaneous application, pump spray for cutaneous application, etc.), patches (tape/plaster, cataplasm/gel patch, etc.), ointments, and the like. When the antioxidant of the present invention is administered orally, examples of the dosage form include tablets, coated tablets, pills, fine granules, granules, powders, capsules, solutions, syrups, emulsions, and suspensions. When the antioxidant of the present invention is administered parenterally, examples of the dosage form include preparations for injection and preparations for infusion. When the antioxidant of the present invention is administered transdermally, examples of the dosage form include topical agents such as patches, embrocations, ointments, creams, and lotions.

The antioxidant of the present invention may include, for example, an additive if necessary, and when the antioxidant of the present invention is used as a pharmaceutical or a pharmaceutical composition, it is preferred that the additive be a pharmaceutically acceptable additive or includes a pharmaceutically acceptable carrier. The additive is not particularly limited, and examples thereof include a base raw material, an excipient, a colorant, a lubricant, a binder, a disintegrant, a stabilizer, a preservative, and a flavoring agent such as a perfume. In the antioxidant of the present invention, the amount of the additive to be blended is not particularly limited as long as it does not hinder the function of the compound of formula (1).

Examples of the excipient include sugar derivatives such as lactose, sucrose, glucose, mannitol, sorbitol, and the like; starch derivatives such as corn starch, potato starch, a starch, dextrin, and the like; cellulose derivatives such as crystalline cellulose; gum arabic; dextran; organic excipients such as pullulan, and the like; silicate derivatives such as light anhydrous silicic acid, synthetic aluminum silicate, calcium silicate, magnesium metasilicate, and the like; phosphates such as calcium hydrogen phosphate, and the like; carbonates such as calcium carbonate, and the like; and inorganic excipients such as sulfates such as calcium sulfate. Examples of the lubricant include stearic acid metal salts such as stearic acid, calcium stearate, magnesium stearate, and the like; talc; polyethylene glycol; silica; and cure[ML1] vegetable oil. Examples of the flavoring agent include perfumes such as cocoa powder, menthol, aromatic powder, mint oil, borneol, cinnamon powder, and the like; sweeteners; and acidulants. Examples of the binder include hydroxypropylcellulose, hydroxypropylmethylcellulose, polyvinylpyrrolidone, and macrogol. Examples of the disintegrant include cellulose derivatives such as carboxymethylcellulose, calcium carboxymethylcellulose, and the like; chemically modified starches such as carboxymethylstarch, sodium carboxymethylstarch, cross-linked polyvinylpyrrolidone, and the like; and chemically modified celluloses. Examples of the stabilizer include paraoxybenzoic acid esters such as methyl paraben, propylparaben, and the like; alcohols such as chlorobutanol, benzyl alcohol, phenylethyl alcohol, and the like; benzalkonium chloride; phenols such as phenol, cresol, and the like; thimerosal; dehydroacetic acid; and sorbic acid.

The compounds represented by the formulae (1) to (15) may be commercially available products or may be prepared in-house based on the production examples in Examples described below.

The antioxidant of the present invention can scavenge reactive oxygen species as described above. Thus, the antioxidant of the present invention can be used as a pharmaceutical for a disease caused by oxidative stress, for example, as described below. Further, the antioxidant of the present invention can be used as an additive in cosmetics, food, and the like, for example.

<Cytoprotective Agent>

The cytoprotective agent of the present invention includes the antioxidant of the present invention as described above. The protective agent of the present invention is characterized in that it includes the antioxidant of the present invention, i.e., a compound represented by the formula (1) or a salt thereof, and other configurations and conditions are not particularly limited. Since the protective agent of the present invention includes the antioxidant of the present invention, reactive oxygen species can be scavenged. Therefore, the cytoprotective agent of the present invention can suppress the cytotoxicity of the reactive oxygen species. Regarding the protective agent of the present invention, reference can be made to the description as to the antioxidant of the present invention.

As to the expression "cytoprotection" in the present invention, it is acceptable as long as cytotoxicity is (significantly) suppressed as compared to the case of absence (non-administration condition) of the cytoprotective agent of the present invention, and the cytotoxicity may be progressed as compared to the initiation (administration initiation). In this case, the "cytoprotection" may also be referred to as "suppression of cytotoxicity," for example. The cytotoxicity can be evaluated, for example, by metabolism, membrane permeability, and the like of cells.

The cell may be, for example, cells collected from a living body, cultured cells, or the like, or may be a cell sheet, a tissue, or an organ composed of cells.

The condition for administering the cytoprotective agent of the present invention is not particularly limited, and for example, an administration form, an administration period, a dosage, and the like can be appropriately determined depending on the type of the subject of administration, and the like. Regarding the subject and condition of administration of the cytoprotective agent of the present invention, reference can be made, for example, to the descriptions as to the subject and condition of administration of the antioxidant of the present invention.

<Pharmaceutical>

A pharmaceutical for a disease caused by oxidative stress of the present invention includes the antioxidant of the present invention as described above. The pharmaceutical of the present invention is characterized in that it includes the antioxidant of the present invention, i.e., a compound represented by the formula (1), and other configurations and conditions are not particularly limited. Since the pharmaceutical of the present invention includes the antioxidant of the present invention, reactive oxygen species generated in vivo can be scavenged. Thus, the pharmaceutical of the present invention can treat a disease caused by oxidative stress. Regarding the pharmaceutical of the present invention, reference can be made to the description as to the antioxidant of the invention.

The expression "treatment" in the present invention may be used in any sense to suppress or prevent the onset of disease, suppress or stop the progression of disease, suppress or stop the progression of disease symptom, and/or improve disease. Thus, the pharmaceutical of the present invention can also be referred to as, for example, an inhibitor, a prophylactic agent, a progression inhibitor, a progression stopping agent and/or an improving agent. In addition, the pharmaceutical of the present invention is applicable as long as the symptoms or progression of the disease is (significantly) suppressed as compared to the case of absence (non-administration condition) of the pharmaceutical of the present invention, and the disease may be progressed as compared to the initiation (administration initiation).

The oxidative stress is, for example, a stress caused by reactive oxygen species, and specific examples thereof include disorders of biomolecules (e.g., a protein, a lipid, a nucleic acid, and the like) and disorders of intracellular organs caused by the reactive oxygen species.

The disease caused by the oxidation stress may be a disease caused only by the oxidative stress, or may be a disease caused by the oxidative stress and other causes. Specific examples of the disease include cerebral infarction, amyotrophic lateral sclerosis, Alzheimer's disease, and Parkinson's disease.

The condition for administering the pharmaceutical of the present invention is not particularly limited, and for example, an administration form, an administration period, a dosage, and the like can be appropriately determined depending on the type of the subject of administration, and the like. Regarding the subject and condition of administration of the pharmaceutical of the present invention, reference can be made, for example, to the description as to the subject and condition of administration of the antioxidant of the present invention.

<Antioxidation Method>

The antioxidation method of the present invention uses the antioxidant of the present invention, as described above. The antioxidation method of the present invention is characterized in that it uses the antioxidant of the present invention, i.e., a compound represented by the formula (1) or a salt thereof, and other steps and conditions are not particularly limited. Since the antioxidation method of the present invention uses the antioxidant of the present invention, reactive oxygen species can be scavenged. Thus, the antioxidation method of the present invention can prevent oxidation of other molecules coexisting, for example. Regarding the antioxidation method of the present invention, reference can be made to the description as to the antioxidant of the present invention.

The antioxidation method of the present invention includes the step of contacting with the antioxidant, for example. More specifically, the antioxidation method of the present invention includes the step of contacting a subject of antioxidation with the antioxidant, for example. The antioxidation method of the present invention may include the step of coexisting with the antioxidant instead of or in addition to the step of contacting. More specifically, in the coexisting, for example, a subject of antioxidation and the antioxidant are allowed to coexist. The coexistence means that, for example, the antioxidant is allowed to simultaneously present in the same agent, the same composition, or a space separated from other component.

The subject of antioxidation is not particularly limited and can be any object.

In the antioxidation method of the present invention, the contacting and the coexisting may be performed, for example, in vitro or in vivo. Regarding the subject and condition of administration of the antioxidant of the present invention, reference can be made, for example, to the description as to the subject and condition of administration in the antioxidant of the present invention.

<Cell Protection Method>

The cell protection method of the present invention uses the cytoprotective agent of the present invention as described above. The protection method of the present invention is characterized in that it uses the cytoprotective agent of the present invention, i.e., a compound represented by the formula (1) or a salt thereof, and other steps and conditions are not particularly limited. Since the protection method of the present invention uses the protective agent of the present invention, reactive oxygen species can be scavenged. Thus, the cell protection method of the present invention can suppress the cytotoxicity of the reactive oxygen species. Regarding the protection method of the present invention, reference can be made to the descriptions as to the antioxidant, protective agent, and antioxidation method of the present invention described above.

The cell protection method of the present invention includes the step of causing cells to coexist with the cytoprotective agent, for example. In the coexisting, the cell and the cytoprotective agent may be brought into contact with each other. In this case, the coexisting may also be referred to as, for example, the contacting.

In the cell protection method of the present invention, the coexisting may be performed, for example, in vitro or in vivo. Regarding the subject and condition of administration of the protective agent of the present invention, reference can be made, for example, to the description as to the subject and condition of administration in the antioxidant of the present invention.

<Treatment Method of Disease Caused by Oxidative Stress>

A method for treating a disease caused by oxidative stress of the present invention (hereinafter, also referred to as "treatment method") includes the step of administering to a patient the pharmaceutical of the present invention. The treatment method of the present invention is characterized in that it administrates the pharmaceutical of the present invention, i.e., a compound represented by the formula (1) or a salt thereof, and other steps and conditions are not particularly limited. Since the treatment method of the present invention uses the pharmaceutical of the present invention described above, reactive oxygen species generated in vivo can be scavenged. Thus, the treatment method of the present invention can treat a disease caused by oxidative stress. Regarding the treatment method of the present invention, reference can be made to the descriptions as to the antioxidant, pharmaceutical, and antioxidation method of the present invention.

The treatment method of the present invention includes the steps of administering the pharmaceutical of the invention, for example. Specifically, the treatment method of the present invention includes the step of administering to a patient the pharmaceutical. The pharmaceutical may be administered in vitro or in vivo. Regarding the subject and condition of administration of the pharmaceutical of the present invention, reference can be made, for example, to the description as to the subject and condition of administration of in the antioxidant of the present invention. The patient may be a patient suffering from the aforementioned disease, a patient predicted to suffer from the disease, or a patient unknown whether to suffer from the disease. The patient may be a patient with a disorder caused by the oxidation stress, a patient predicted to suffer from a disorder caused by the oxidative stress, or a patient unknown whether to suffer from a disorder caused by the oxidative stress.

<Novel Compound>

The pyrazole ring derivative or a salt thereof of the present invention is represented by the following formula (4):

(4)

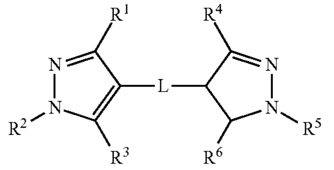

In the formula (4), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is an alkyl group having 2 or more carbon atoms, $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is an alkyl group having 2 or more carbon atoms, $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and L is a saturated or unsaturated hydrocarbon group.

The pyrazole ring derivative or a salt thereof of the present invention is characterized in that it is represented by the formula (4), and other configurations and conditions are not particularly limited. Regarding the pyrazole ring derivative or a salt thereof of the present invention, reference can be made to the descriptions as to the antioxidant, pharmaceutical, and antioxidation method of the present invention.

<Use of Compound or Salt Thereof>

The present invention is the use of a compound represented by the formula (1) or a salt thereof for use in cell protection, a compound represented by the formula (1) or a salt thereof for use in antioxidation, and a compound represented by the formula (1) or a salt thereof for use in treatment of a disease caused by oxidative stress. In addition, the present invention is the use of a compound represented by the formula (1) or a salt thereof for producing an antioxidant, a compound represented by the formula (1) or a salt thereof for producing a cytoprotective agent, and a compound represented by the formula (1) or a salt thereof for producing a pharmaceutical for a disease caused by oxidative stress. Regarding the use of the present invention, reference can be made, for example, to the descriptions as to the antioxidant, protective agent, pharmaceutical, antioxidation method, cell protection method, and treatment method of the present invention.

EXAMPLES

Next, examples of the present invention will be described. The present invention, however, is not limited by the following Examples. Commercially available reagents were used based on their protocols unless otherwise mentioned.

Example 1

A compound included in the antioxidant of the present invention was synthesized.

(1) Synthesis of ED2AP 3.58 g of 3-methyl-1-phenyl-5-pyrazolone (hereinafter, also referred to as "edaravone"), 2.59 g of malonaldehyde dianilide hydrochloride, and 20 ml of ethanol were added to a reactor and dissolved. To the obtained solution, 2.04 g of triethylamine and 0.4 ml of water were added and stirred for 1 hour at room temperature (about 25° C., hereinafter, the same applies). After the stirring, the resultant was further reacted for 1 hour at 50° C. After discharging the obtained reaction solution to 100 ml of 1N hydrochloric acid, the mixture was sufficiently stirred and the precipitate was filtered. The resulting cake was washed with water. The cake was added to 200 ml of an aqueous sodium hydroxide solution having a 1% by weight concentration and completely dissolved by heating with stirring. Next, the dissolved solution was stirred for 3 hours after cooling to room temperature. Then, the liquid containing the obtained precipitate was filtered, and then the cake was washed with water. This resulted in 2.99 g of dark red crystal of ED2AP having the following physical properties. Note that the melting point of ED2AP was 249° C., which was water-soluble.

$^1$H-NMR (nuclear magnetic resonance) (600 MHz, Internal Standard: THF (tetrahydrofuran)-d8, AV-600 (Bruker)): δ2.33 (s, 6H), 6.92 (d, 2H), 7.02 (m, 2H), 7.21 (m, 4H), 8.01 (m, 4H), 8.31 (t, 1H)

(2) Synthesis of Compound of Formula (10)

3 ml of dimethylformamide was added to a reactor and the exterior of the reactor was cooled with ice water. 1.75 g of phosphorus oxychloride was slowly dropped into the reactor (Reaction Solution A). In another reactor, 1.78 g of edaravone was dissolved in 5 ml of dimethylformamide (Reaction Solution B). Under room temperature, the reaction solution B was slowly added to the reaction solution A, and the resulting mixture was allowed to react for 1 hour with the end of addition (Reaction Solution C) being a reference. In another reactor, 1.81 g of 3-methyl-1-phenyl-5-pyrazolone was added to 8 ml of chloroform and dissolved (Reaction Solution D). Under room temperature, the reaction solution C was slowly added to the reaction solution D, followed by stirring for 20 minutes and further stirring at 70° C. for 1 hour. To the resultant, 0.2 g of water was added and stirred for another 2 hours. The obtained reaction solution was discharged into 100 ml of water and extracted with a mixed solvent of toluene/ethyl acetate=1/1 (volume ratio). After condensation of the obtained extract, column purification was performed to obtain 2.92 g of yellow crystal of the compound of the formula (10) having the following physical properties. Note that the melting point of the compound of the formula (10) was 177° C., which was poorly soluble in water.

$^1$H-NMR (nuclear magnetic resonance) (600 MHZ, Internal Standard: $CDCl_3$, AV-600 (Bruker)): δ 2.33 (s, 6H), 7.20 (s, 1H), 7.26 (m, 2H), 7.43 (m, 4H), 7.90 (dd, 4H)

(3) Synthesis of Compound of Formula (14)

1.00 g of edaravone, 0.72 g of paraformaldehyde, and 20 ml of formic acid were added to a reaction flask and stirred overnight for 20 hours at 70° C. The obtained reaction solution was discharged into 80 ml of water and extracted with a mixed solvent of toluene/ethyl acetate=1/1 (volume ratio). When the extract was condensed to about two-thirds, crystals were precipitated. Further, the resultant was cooled to room temperature, and sufficiently crystallized, and then filtered. The obtained cake was washed with toluene to obtain 0.88 g of pale yellow crystal of the compound of the formula (14) having the following physical properties. Note that the compound of the formula (14) was poorly soluble in water.

$^1$H-NMR (nuclear magnetic resonance) (600 MHz, Internal Standard: DMSO (dimethylsulfoxide)-d6, AV-600 (Bruker)): δ2.31 (s, 6H), 3.43 (s, 2H), 7.32 (m, 2H), 7.48 (m, 4H), 7.70 (m, 4H)

(4) Synthesis of BisEp-C3

In Example 1(1), synthesis was performed in the same manner as described above except that 3-methyl-1-ethyl-5-pyrazolone was used instead of edaravone to obtain red crystal of BisEp-C3 having the following physical properties. Note that BisEp-C3 was water-soluble.

$^1$H-NMR (nuclear magnetic resonance) (600 MHZ, DMSO (dimethylsulfoxide)-d6, AV-600 (Bruker)): δ 1.18 (t, 6H), 2.19 (s, 6H), 3.69 (q, 4H), 7.29 (d, 2H), 8.00 (t, 1H)

(5) Synthesis of BisEp-C1

In Example 1(2), synthesis was performed in the same manner as described above except that 3-methyl-1-ethyl-5-pyrazolone was used instead of edaravone to obtain yellow crystal of BisEp-C1 having the following physical properties. Note that BisEp-C1 was water-soluble.

$^1$H-NMR (nuclear magnetic resonance) (600 MHz, DMSO (dimethylsulfoxide)-d6, AV-600 (Bruker)): δ1.24 (t, 6H), 2.23 (t, 6H), 3.79 (q, 4H), 7.33 (s, 1H)

(6) Synthesis of BisEp-C1 ($H_2$)

In Example 1(3), synthesis was performed in the same manner as described above except that 3-methyl-1-ethyl-5-pyrazolone was used instead of edaravone, then the obtained reaction solution was condensed, and the resultant was subjected to column purification to obtain colorless crystal of BisEp-C1 ($H_2$) having the following physical properties. Note that BisEp-C1 ($H_2$) was water-soluble.

$^1$H-NMR (nuclear magnetic resonance) (600 MHz, DMSO (dimethylsulfoxide)-d6, AV-600 (Bruker)): δ1.18 (t, 6H), 2.09 (t, 6H), 3.04 (s, 2H), 3.73 (q, 4H)

Example 2

It was examined that the decomposition of the antioxidant of the present invention in water and an aqueous solvent is suppressed, that is, the antioxidant of the present invention has storage stability.

The storage stability of edaravone, EMPO, ED2AP, and BisEp-C3 of the following formula (A) were examined. Specifically, edaravone, EMPO, ED2AP, and BisEp-C3 were dissolved in pH7.4-PBS or pure water so as to have a final concentration of 200 μmol/l to prepare dissolved solutions of these compounds. When the compounds were difficult to be dissolved, they were dissolved in an ultrasonic cleaner with warm water at 40° C.

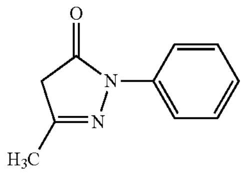

Edaravone

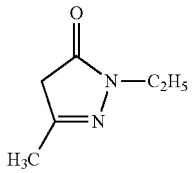

EMPO

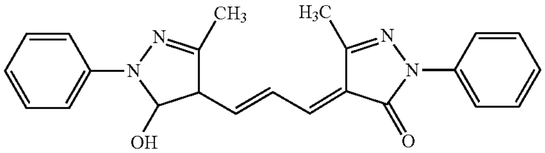

ED2AP

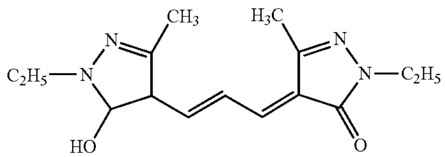

BisEp-C3

Under the measurement conditions for HPLC described below, the initial concentration was quantified, and then each solution was stored in an oven, which was protected from light, at 37° C., and quantified under the same measurement conditions after 1 week and 2 weeks, to determine residual rate (%) with the initial concentration (100%) being a reference. The results are shown in Table 1 below.

Measurement conditions for HPLC

Equipment:

- High Performance Liquid Chromatography (Shimadzu Corporation)
- Data processing software (Model: LCsolution Ver. 1.0, produced by Shimadzu Corporation)
- Pump (Model: LC-20AD; produced by Shimadzu Corporation)
- Column oven (Model: CTO-20A; produced by Shimadzu Corporation)
- Autosampler (Model: SIL-20A; produced by Shimadzu Corporation)
- PDA detector (Format: SPD-M20A)

HPLC Assay Conditions:

- Column: Atlantis dC18 5 μm (250×4.6 mm I.D.; produced by Waters)
- Column temperature: 45° C.
- Flow rate: 0.5 mL/min
- Detection method: UV (254 nm)
- Eluate A: pH3 buffer solution (adjusted to pH3 by adding phosphoric acid to 0.05M $KH_2PO_4$ aqueous solution)/methanol=90/10
- Eluate B: methanol
- Eluate C: acetonitrile
- Time Program (gradient):

| | Time (min) | | | | |
|---|---|---|---|---|---|
| | 0 | 10 | 20 | 45 | 50 |
| Eluate A (%) | 100 | 100 | 80 | 30 | 30 |
| Eluate B (%) | 0 | 0 | 20 | 20 | 20 |
| Eluate C (%) | 0 | 0 | 0 | 50 | 50 |

TABLE 1

| | | Residual rate (%) | | |
|---|---|---|---|---|
| Solution | Substance name | Initial concentration | After 1 week | After 2 weeks |
| pH 7.4-PBS | Edaravone | 100 | 31.2 | 0.2 |
| | EMPO | 100 | 0.0 | 0.0 |
| | ED2AP | 100 | 96.2 | 91.3 |
| | BisEp-C3 | 100 | 98.7 | 93.6 |
| Pure water | Edaravone | 100 | 82.8 | 80.4 |
| | EMPO | 100 | 6.3 | 1.4 |
| | ED2AP | 100 | 96.1 | 89.8 |
| | BisEp-C3 | 100 | 99.4 | 88.5 |

As shown in the Table 1, it was found that ED2AP and BisEp-C3 have a higher residual rate and excellent storage stability as compared to edaravone and EMPO in both the cases of storing in pure water and a phosphate buffer. In particular, ED2AP and BisEp-C3 have extremely high storage stability in a phosphate buffer as compared to edaravone and EMPO, which shows that they are suitable as pharmaceuticals to be stored in aqueous solvents.

This showed that the decomposition of the antioxidant of the present invention in water and an aqueous solvent is suppressed, that is, the antioxidant of the present invention has storage stability.

Example 3

It was examined that the antioxidant of the present invention has an eliminating ability for non-radical species such as singlet oxygen before and after storage in an aqueous solvent.

The ESR method was used to track changes in singlet oxygen-eliminating ability in PBS solutions of edaravone, EMPO, ED2AP, and BisEp-C3. Specifically, the following reaction system was utilized. First, PBS solutions containing Pterin-6-carboxylic acid (30 μmol/l) and 4-oxo-TEMP (4 mmol/l) are irradiated with a 200 W mercury xenon lamp (hv, RUVF-203S) for 5 seconds using a band-pass filter of 340 nm. Then, in the reaction system, singlet oxygen ($^1O_2$) is generated by the following actions.

$$\text{Pterin-6-carboxylic acid} + h\nu \rightarrow \text{Pterin-6-carboxylic acid*}$$

$$\text{Pterin-6-carboxylic acid*} + {}^3O_2 \rightarrow \text{Pterin-6-carboxylic acid} + {}^1O_2$$

Next, the resulting singlet oxygen reacts with 4-oxo-TEMP added to the reaction system as shown in the following formula (B), resulting in a nitroxide which is a stable radical detectable by ESR. This radical causes a triplet derived from N (nitrogen atom) in the ESR spectrum as shown in (A) in FIG. 1.

[formula B]

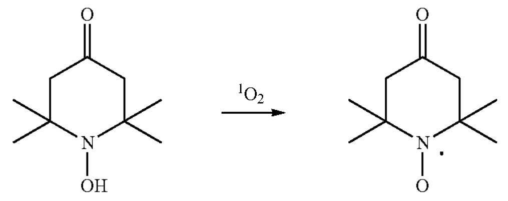

4-Oxo-2,2,6,6-tetramethylpiperidine (4-oxo-TEMP)

4-Oxo-2,2,6,6-tetramethylpiperidine-N-oxyl (4-oxo-TEMPO) Stable radical

When edaravone, EMPO, ED2AP, or BisEp-C3 is added to the reaction system, the intensity of the signal obtained by ESR changes. Thus, the singlet oxygen-eliminating ability of each compound can be examined based on the following formula (C).

[formula C]

$$O_2{}^3 \xrightarrow{hv} O_2{}^1$$

$$O_2{}^1 + \text{4-oxoTEMP} \xrightarrow{k_1} \text{4-oxoTEMPO (Observable by ESR)}$$

$$O_2{}^1 + \text{Evaluation reagent} \xrightarrow{k_2} \text{Product not observed by ESR}$$

$$-d[\text{4-oxoTEMP}]/dt = d[\text{4-oxo-TEMPO}]/dt = k_1\,[\text{4-oxo TEMP}][O_2{}^1]$$

$$-d[\text{Evaluation reagent}]/dt = d[\text{Product}]/dt = k_2\,[\text{Evalutation reagent}][O_2{}^1]$$

$1_0$: 4-oxo-TEMP signal intensity obtained without antioxidant

1: 4-oxo-TEMPO signal intensity obtained when evalution reagent is added

I: Proportional to amount of 4-oxo-TEMPO $I_0$-I: Proportional to product not observed by ESR -continued $(I_0-I) / I = k_2[\text{Evaluation reagent}][O_2{}^1]/k_1[\text{4-oxoTEMP}][O_2{}^1]$ $[\ ]_0$: Concentration at start of reaction $(I_0-I)/I = k_2 / k_1 \bullet [\text{Evaluation reagent}]_0/[\text{4-oxoTEMP}]_0$ The prepared PBS solutions of edaravone, EMPO, ED2AP, and BisEp-C3 were stored and examined for the singlet oxygen-eliminating ability over time in the same manner as in Example 2. The ESR measurement conditions were as follows. In addition, the singlet oxygen-eliminating ability was calculated as a relative value with the eliminating ability at day 0 being a reference.

Measurement Conditions for ESR

Equipment:

Electron spin resonance spectrometer (JES-TE-300, produced by Japan Electron Optics Laboratory Co. Ltd.)

Measurement Conditions:

Microwave output: 8 mW

Sweep time: 1 minute

Sweep width: 335.5±5 mT

Magnetic field modulation: 100 kHz 0.079 mT

Gain: ×630

Time constant: 0.03 sec

Figure 1B:
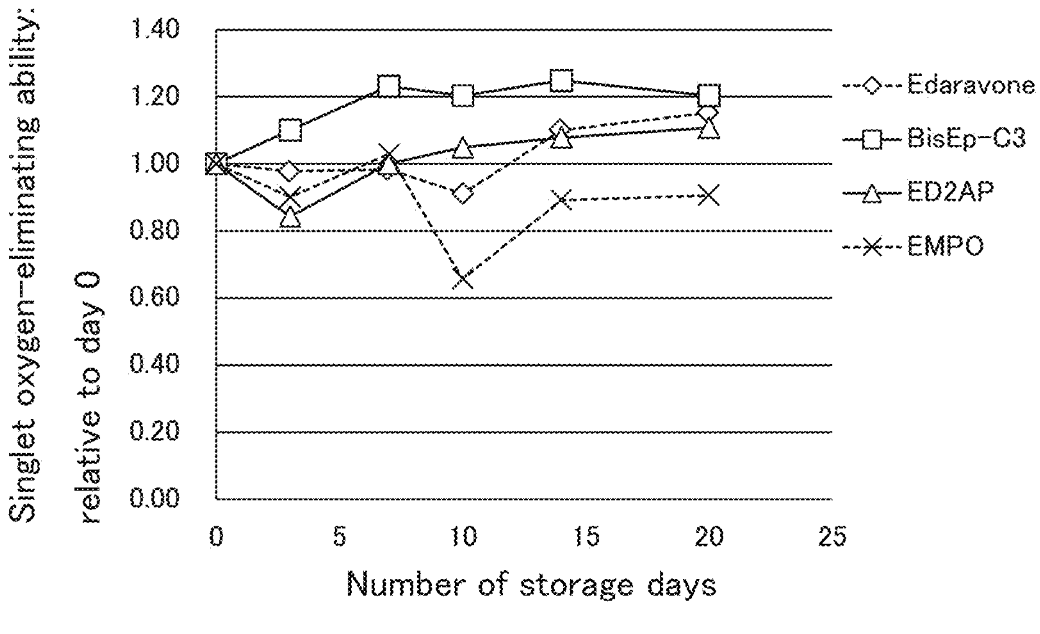

The results are shown in FIG. 1. FIG. 1 shows graphs showing ESR results. In FIG. 1, (A) is a graph showing a triplet derived from N (nitrogen atom) in the ESR spectrum, and (B) is a graph showing the results of ESR of each compound. In (B) in FIG. 1, the horizontal axis indicates the number of storage days, and the vertical axis indicates the relative value of the singlet oxygen-eliminating ability with the start of storage (day 0) being 1. As shown in (B) in FIG. 1, for any of the compounds, the singlet oxygen-eliminating ability after storage did not differ greatly from that at the start of storage. These results showed that the antioxidant of the present invention had an eliminating ability for a non-radical species such as singlet oxygen before and after storage in an aqueous solvent. These results also suggested that the products of edaravone and EMPO after decomposition have the singlet oxygen-eliminating ability.

Example 4

It was examined that the antioxidant of the present invention has an eliminating ability for radical species such as superoxide anion.

For examining the reactive oxygen-eliminating effect of the antioxidant of the present invention, the superoxide produced by the neutrophils when the neutrophils isolated from the peripheral blood of healthy individuals were stimulated with PMA (phorbor-12-myristate-13-acetate) was used. The superoxide production amount was measured by chemiluminescence using CLA (2-methyl-6-pjenyl-3, 7-dihydroimidazo[1,2-a]pyrazine-3-one).

First, ED2AP, BisEp-C3, edaravone, BisEp-C1, or BisEp-C1 ($H_2$) was added to a neutrophil of $4\times10^5$ cells per sample so as to achieve a predetermined concentration (0, 12.5, 25, 50, 100, or 200 μmol/l, or 0, 125, 250, 500, 1250, 2500, or 5000 μmol/l) with 5 μmol of CLA, and then the cell suspension was seeded in flat-bottomed 96-well plates. The volume of the suspension was 200 μl/well, and phenol red free Ca+, Mg+ HBSS was used as the solution. In addition, the neutrophil was stimulated by adding PMA so as to achieve a concentration of 100 ng/ml. After the stimulation, a plate reader (Envision 2104 Multilabel Reader, produced by Perkin Elmer Co., Ltd.) was used to measure the chemiluminescence value over time for 30 minutes with the PMA stimulation time being a reference. The measurement interval was 30 seconds. The sum of the chemiluminescence values obtained every 30 seconds for 30 minutes was taken as the superoxide production amount. In addition, as a control, the superoxide production amount was measured in the same manner except that each compound was not added. The relative value of the superoxide production amount when each compound was added was calculated with the superoxide production amount of the control being 100. The results are shown in FIG. 2.

Figure 2A:
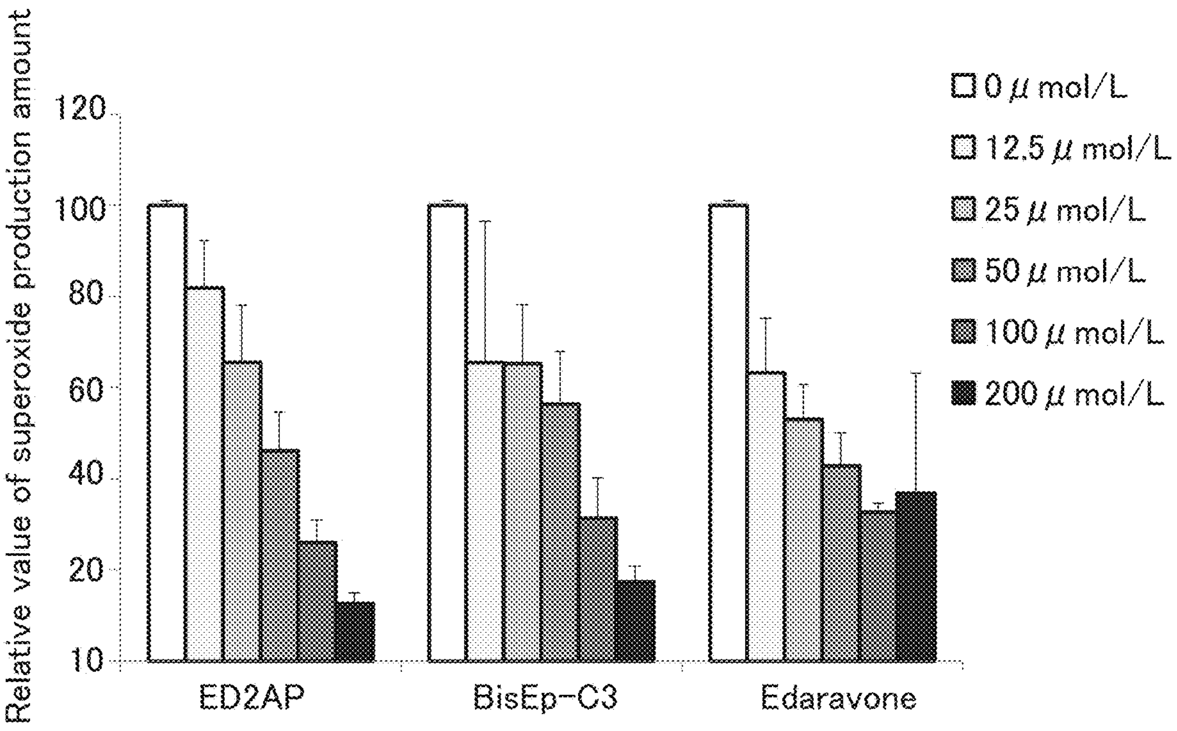
FIG. 2 shows graphs showing the relative value of the superoxide production amount in Example 4.
Figure 2B:
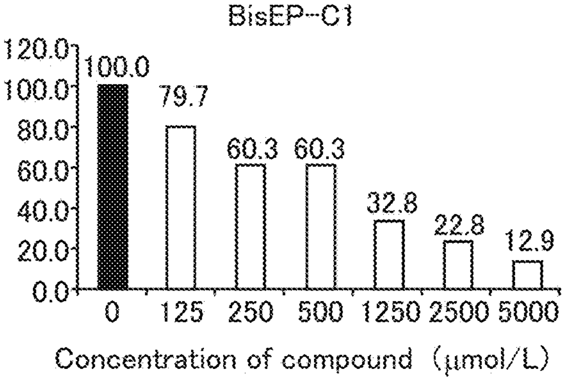
Figure 2C:
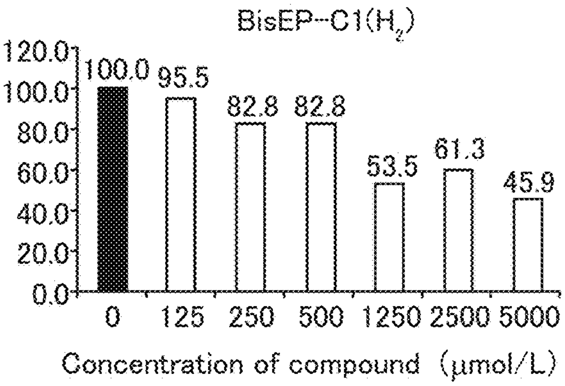

FIG. 2 shows graphs showing the relative values of the superoxide production amount, (A) is a graph showing the results of ED2AP, BisEp-C3, and edaravone, (B) is a graph showing the results of BisEp-C1, and (C) is a graph showing the results of BisEp-C1 ($H_2$). In FIG. 2, the horizontal axis indicates the type of the compound or the concentration of the compound, and the vertical axis indicates the relative value of the superoxide production amount. As shown in FIG. 2A to 2C, any of the compounds suppressed the superoxide production amount in a concentration-dependent manner, i.e., showed the reactive oxygen species-eliminating ability. Among the above compounds, ED2AP and BisEp-C3 remarkably suppressed superoxide production amount, and the reactive oxygen species-eliminating ability is more potent than edaravone at high concentrations. These results showed that the antioxidant of the present invention has an eliminating ability for radical species such as superoxide anion.

Example 5

It was examined that the antioxidant of the present invention alleviates the cytotoxicity of the reactive oxygen species, that is, has a cytoprotective function.

Edaravone, ED2AP and BisEp-C3 were examined whether they had the function of alleviating neuronopathy. Specifically, singlet oxygen was generated by combining Rose Bengal (RB), which is a sensitizer, with green light (G-LED), and the function of alleviating the cytotoxicity of the generated singlet oxygen was examined with the cellular activity being an indicator.

First, rat neuroid cells B50 were cultured in 12-well dishes at $2\times10^5$ cells/well (medium: RPMI-1640 medium containing 5% FCS) overnight. After the culturing, the medium of each well was replaced with HBSS (1000 μl/well; phenol red free Ca+, Mg+) containing 200 nmol/l RB and edaravone, ED2AP, or BisEp-C3 having a predetermined concentration (0, 12.5, 25, 50, or 100 μmol/l). The dish was then irradiated with G-LED for 5 minutes to generate singlet oxygen. Thereafter, the medium of each well was replaced with 1000 μl of HBSS and Alamar Blue was added. The dish was then allowed to react for about 2 hours in an incubator at 37° C. and 5% $CO_2$. After the reaction, fluorescence intensity (excitation wavelength: λ-560 nm, fluorescence wavelength: λ-595 nm) was measured with a plate reader (infinite200, Tecan Trading AG). In this experimental system, the higher the cellular activity, the more Alamar Blue is taken up and the higher the fluorescence intensity. As a control, fluorescence intensity was measured in the same manner except that sodium azide (Azide, $NaN_3$) was added instead of the compounds so as to achieve a concentration of 4 mmol/l. As a negative control (NC), fluorescence intensity was measured in the same manner except that RB was not added. The relative value of the fluorescence intensity in the sample to which each compound was added was calculated with the fluorescence intensity of the negative control being 100. The results are shown in FIG. 3.

Figure 3:
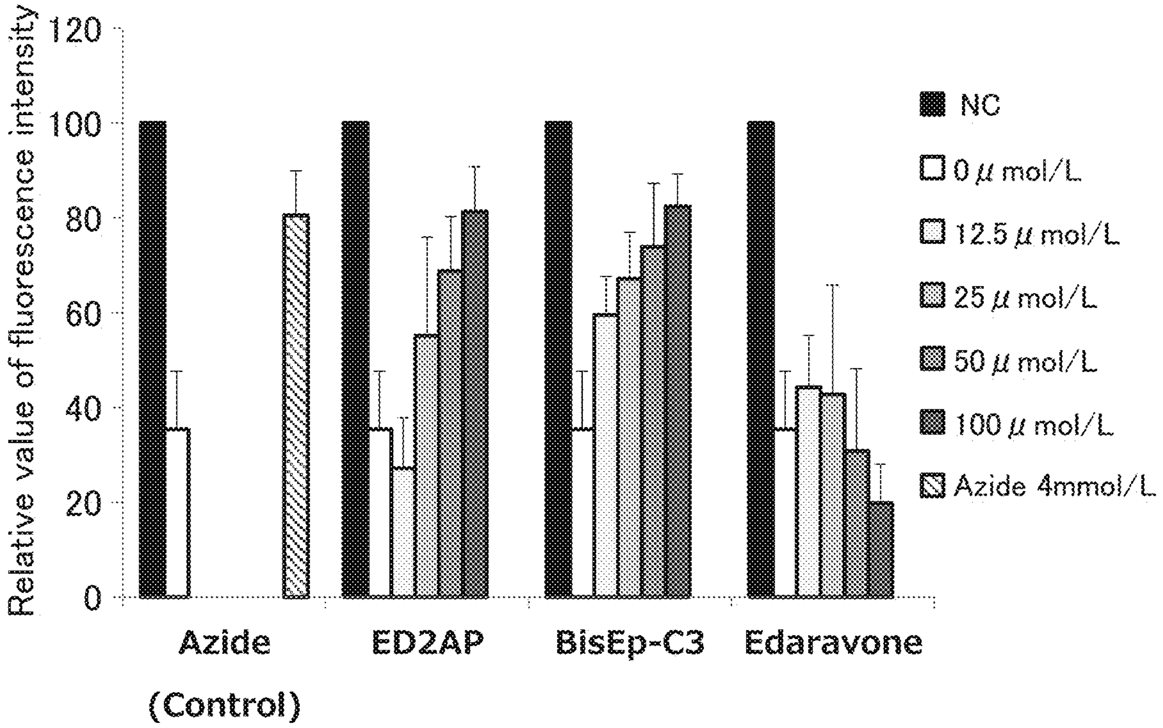
FIG. 3 is a graph showing the relative value of the fluorescence intensity in Example 5.

FIG. 3 is a graph showing the relative value of the fluorescence intensity. In FIG. 3, the horizontal axis indicates the type of the compound or the concentration of the compound, and the vertical axis indicates the relative value of the fluorescence intensity. As shown in FIG. 3, when the fluorescence intensity of the sample subjected to only G-LED irradiation without adding RB was set to 100, in the sample to which RB was added and subjected to G-LED irradiation, cell death due to the generated singlet oxygen is induced, and its fluorescence intensity was reduced to 33.17 (control). On the other hand, when sodium azide (Azide) having a singlet oxygen-eliminating effect was added, the fluorescence intensity was recovered to 80.81. When ED2AP and BisEp-C3 were added, the fluorescence intensity was recovered in a concentration-dependent manner. In contrast, the fluorescence intensity was not recovered in edaravone. These results showed that the antioxidant of the present invention alleviates the cytotoxicity of the reactive oxygen species, that is, has a cytoprotective function. Furthermore, it was found that the cytoprotective function of ED2AP and BisEp-C3 was higher than that of edaravone.

Example 6

It was examined that the antioxidant of the present invention has an eliminating ability for radical species such as superoxide before and after storage in an aqueous solvent.

PBS solutions of ED2AP, BisEp-C3, and edaravone were prepared in the same manner as in Example 2 and stored for 10 days. The superoxide production amount was calculated in the same manner as in Example 4 except that the PBS solution after storage was added instead of ED2AP, BisEp-C3, edaravone, BisEp-C1 or BisEp-C1 ($H_2$) so as to achieve a predetermined concentration (0, 6.25, 12.5, 25, 50, 100 or 20 μmol/l) of ED2AP, BisEp-C3 or edaravone. Further, PBS solutions of ED2AP, BisEp-C3, and edaravone were prepared in the same manner as in Example 2, and the superoxide production amount was calculated in the same manner except that the PBS solution immediately after preparation was used. Then, the relative value of the superoxide production amount of each sample was calculated with the superoxide production amount of the sample of 0 μmol/l being 100. The results are shown in FIG. 4.

Figure 4A:
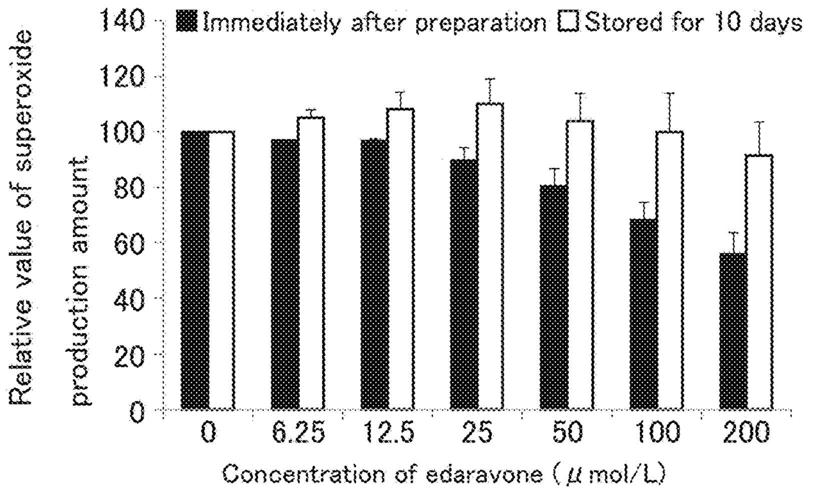
FIG. 4 shows graphs showing the relative value of the superoxide production amount in Example 6.
Figure 4B:
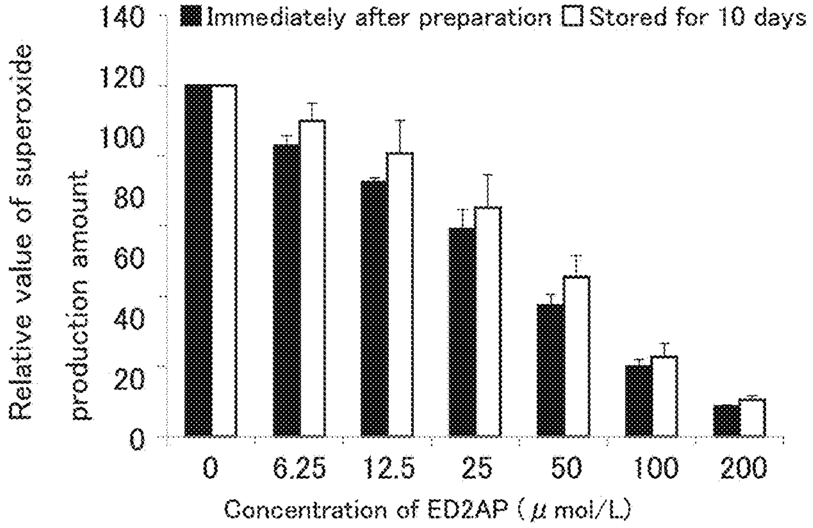
Figure 4C:
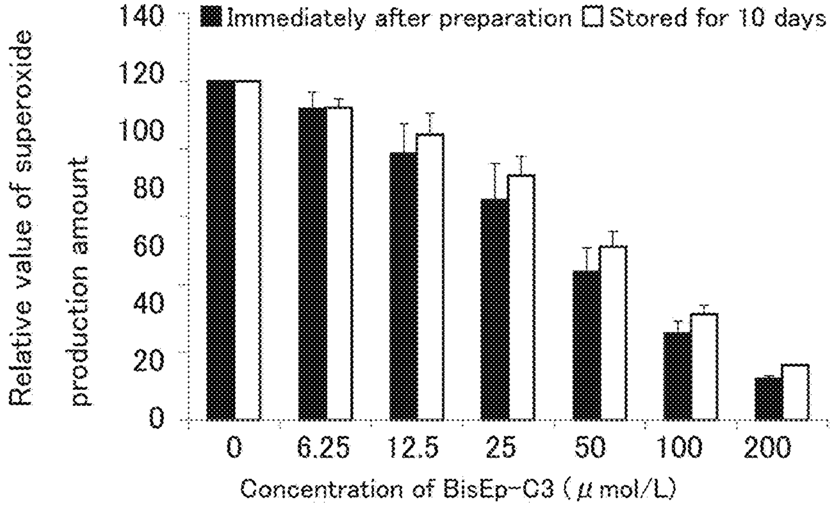

FIG. 4 shows graphs showing the relative value of the superoxide production amount. In FIG. 4, (A) shows the result of edaravone, (B) shows the result of ED2AP, and (C) shows the result of BisEp-C3. As shown in (A) in FIG. 4, the superoxide-eliminating ability of edaravone was remarkably lowered after storage for 10 days. In contrast, ED2AP and BisEp-C3 maintained the superoxide-eliminating ability equivalent to that immediately after preparation even after storage. This showed that the antioxidant of the present invention has an eliminating ability for radical species such as superoxide before and after storage in an aqueous solvent.

Example 7

It was examined that the antioxidant of the present invention has low cytotoxicity and that the byproduct obtained after reacting the antioxidant of the present invention with singlet oxygen has low cytotoxicity.

(1) Toxicity Evaluation

Rat neuroid cells B50 were seeded in 12-well plates and then cultured. Edaravone (RC), ED2AP, or BisEp-C3 was added to each well so as to achieve a predetermined concentration (12.5, 25, 50, 100, or 200 μmol/l), and then incubated for 24 hours at 37° C. and 5% $CO_2$. Cell viability in each well after the culture was measured using Alamar Blue. The results are shown in FIG. 5.

Figure 5:
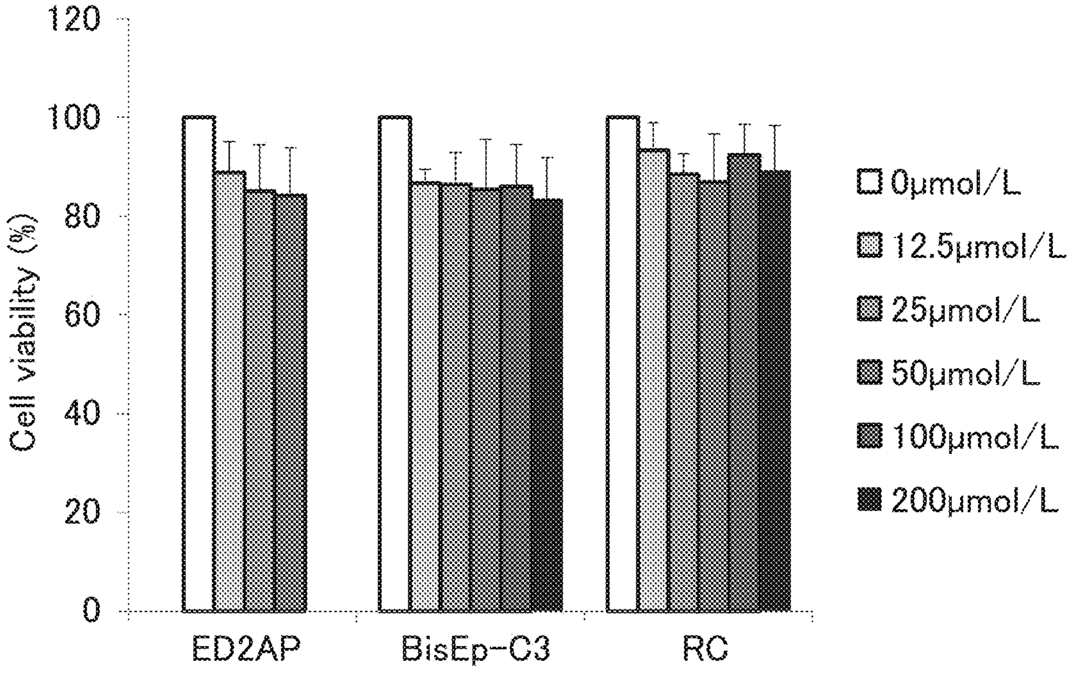
FIG. 5 is a graph showing the cell viability in Example 7.

FIG. 5 is a graph showing the cell viability. In FIG. 5, the horizontal axis indicates the type of the compound or the concentration of the compound, and the vertical axis indicates the cell viability. As shown in FIG. 5, edaravone, ED2AP, and BisEp-C3 were not cytotoxic at any concentration.

(2) Toxicity Evaluation on Byproducts

In a cell-free system, the RB was added to media (50% FCS-containing RPMI-1640 media) containing edaravone, ED2AP, and BisEp-C3 having a predetermined concentration (50, 100, or 200 μmol/l) and then irradiated with LED (G-LED) at 525 nm to generate singlet oxygen, whereby reacting each compound with singlet oxygen. The cell viability was measured in the same manner as in Example 7(1), except that the culture solution after the reaction was used as a medium of the neuroid cell B50. As a negative control (NC), the cell viability was measured in the same manner except that each compound and PB were not added in the cell-free system. Further, as a control (RB), the cell viability was measured in the same manner except that each compound was not added and only PB was added in the cell-free system. The results are shown in FIG. 6.

Figure 6:
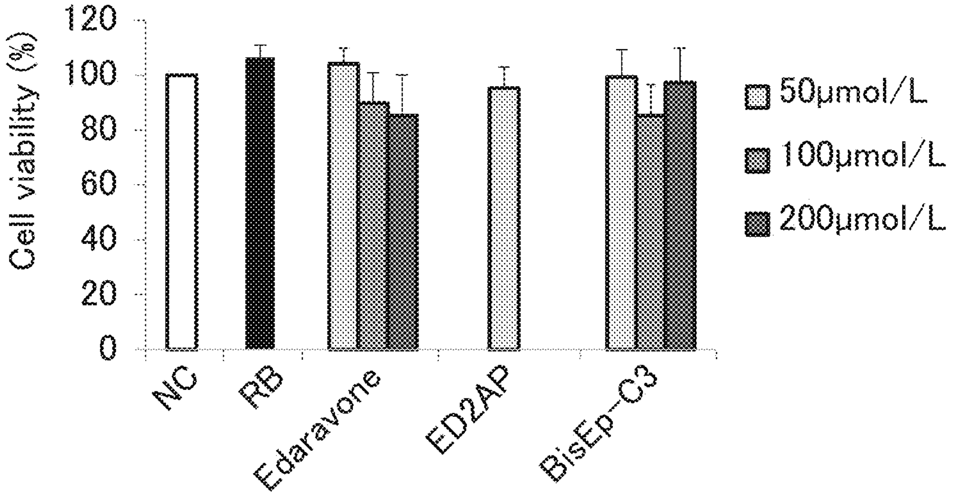
FIG. 6 is a graph showing the cell viability in Example 7.

FIG. 6 is a graph showing the cell viability. In FIG. 6, the horizontal axis indicates the type of the compound or the concentration of the compound, and the vertical axis indicates the cell viability. As shown in FIG. 6, the byproducts of edaravone, ED2AP, and BisEp-C3 were not cytotoxic at any concentration.

These results showed that the antioxidant of the present invention has low cytotoxicity and that the byproduct obtained after reacting the antioxidant of the present invention with singlet oxygen has low cytotoxicity.

Example 8

It was examined that the compound included in the antioxidant of the present invention forms a conjugated system and has a tautomer.

(1) ED2AP

ED2AP was dissolved in $CDCl_3$ or DMSO and a $^1$H-NMR spectrum was acquired using a NMR device (AV-600, Bruker). When $CDCl_3$ was used as a solvent, the frequency was 600 MHz, the compound concentration was 20 mg/ml, the temperature was 333 K, and the internal standard was tetramethylsilane. When DMSO was used as a solvent, the measurement conditions were the same as those in the case of using $CDCl_3$ as a solvent except that the temperature was 298 K. The results are shown in FIG. 7.

Figure 7A:
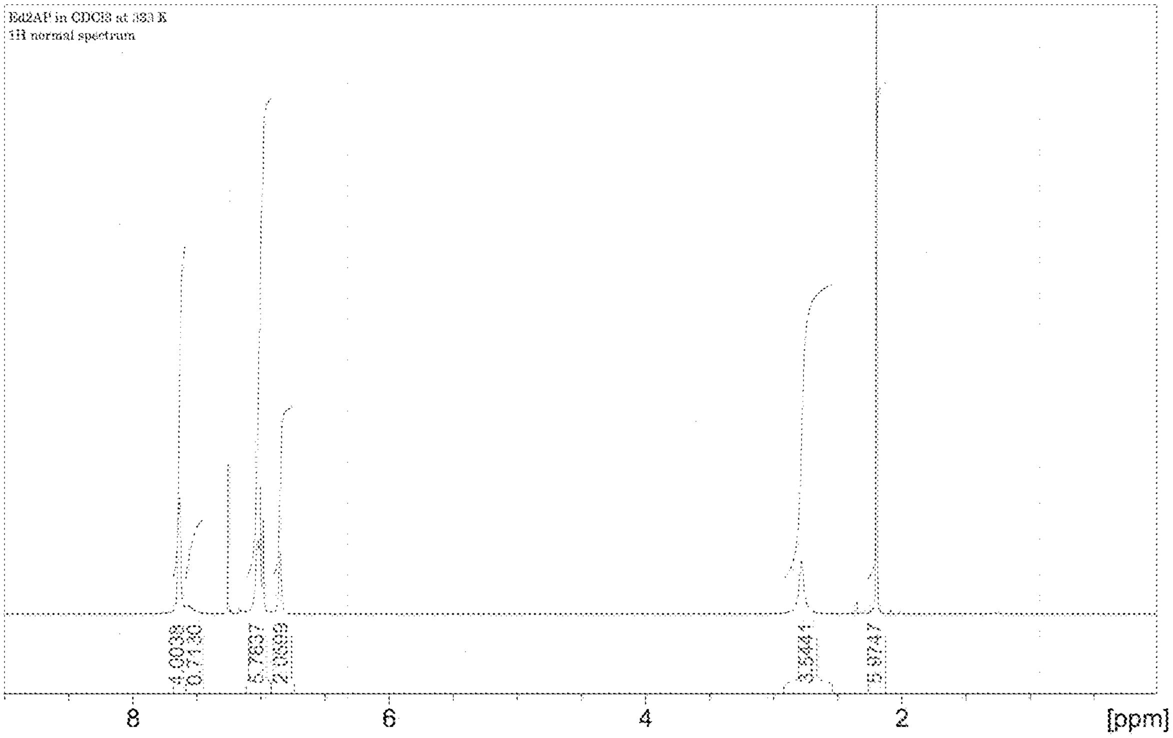
FIG. 7 shows graphs showing the $^1$H-NMR spectrum in Example 8.
Figure 7B:
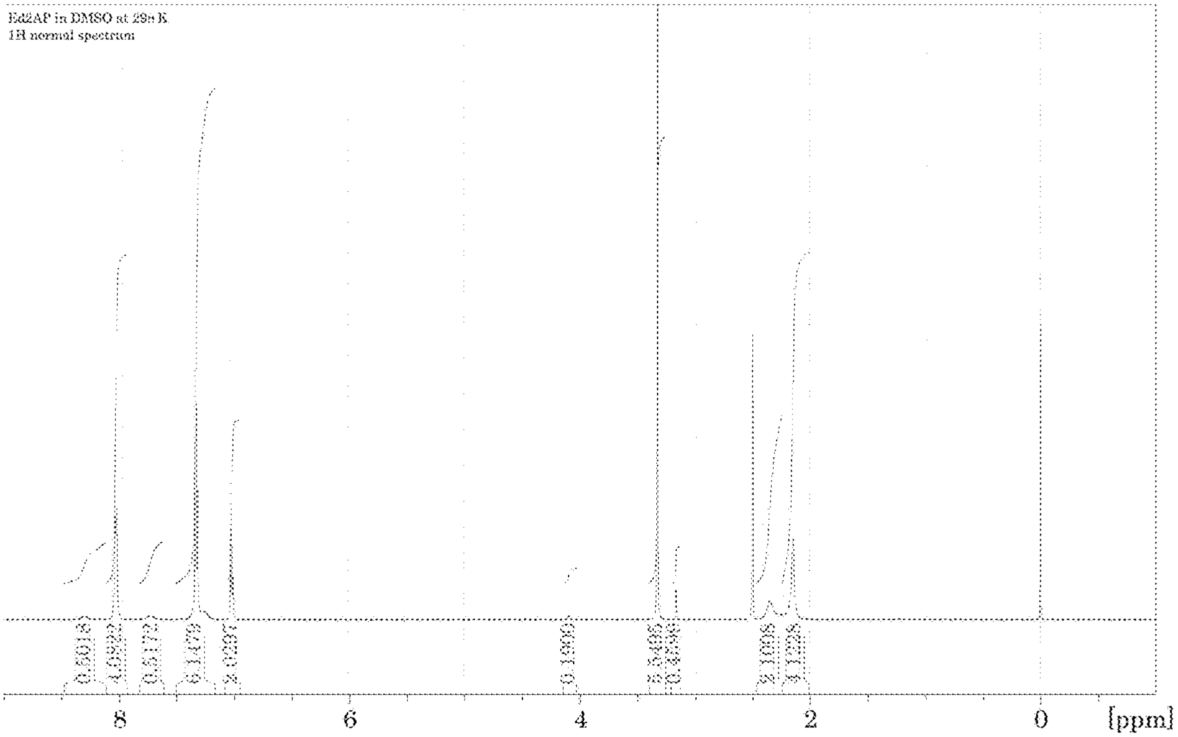

FIG. 7 shows graphs showing a NMR spectrum. In FIG. 7, (A) shows the result when $CDCl_3$ was used, and (B) shows the result when DMSO was used. In FIG. 7, the horizontal axis indicates the chemical shift value, and the vertical axis indicates the relative intensity. As shown in FIG. 7, three signals (8.02, 7.33, and 7.03) of the benzene ring and signals of three protons bonded to the conjugated double bond of the crosslinking part have been observed to be broad by chemical exchange by keto-enol rearrangement, and it was found that the linker region (L) forms a conjugated system. Also, of the three protons, one proton in the center was observed in two portions at 8.30 ppm and 7.74 ppm at the lowest magnetic field, and two protons close to edaravone at both ends were observed at 7.32 ppm and 7.26 ppm, and the effect also appears on the methyl group, resulting in two signals (2.35 and 2.15 ppm). These showed that an isomer of cis-cis, cis-trans, trans-cis, or trans-trans was formed by the two double bonds of L. From these, it was found that, since the keto-enol isomerism occurs and the position of the double bond moves between neighboring atoms in the hydroxy group of $R^3$, ED2AP forms a tautomer of the following formula D and a geometric isomer (cis-trans isomer) of these.

[formula D]

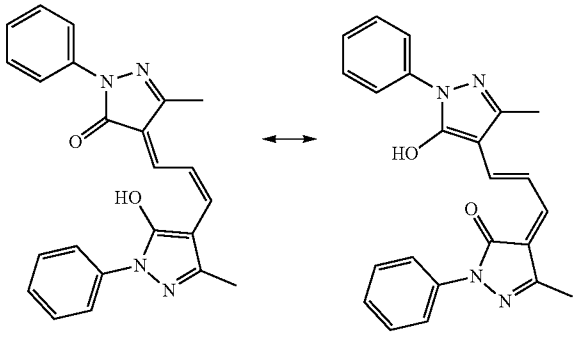

Tautomer (2) BisEp-C3

BisEp-C3 (Bis-MP-C3) was dissolved in $CDCl_3$, and the $^1$H-NMR spectrum and the $^{13}$C-NMR spectrum were acquired using the NMR device. In acquiring the $^1$H-NMR spectrum, the frequency was 600 MHz, the compound concentration was 20 mg/ml, the temperature was 298 K or 313 K, and the internal standard was tetramethylsilane. In acquiring the $^{13}$C-NMR spectrum, the measurement conditions were the same as those in the case of acquiring the $^1$H-NMR spectrum except that the temperature was 298 K and the frequency was 150 MHz. The chemical shift value and the J coupling value were also calculated based on the $^1$H-NMR spectrum and the $^{13}$C-NMR spectrum. The results are shown in FIGS. 8 and 9 and Table 2.

TABLE 2

| | | 1H (ppm) | Integral value | J | 13C (ppm) |
|---|---|---|---|---|---|
| 2-ethyl group | CH3 | 1.29 | 6 | t 7.2 Hz | 14.1 |
| 2-ethyl group | CH2 | 3.85 | 4 | q 7.2 Hz | 39.7 |
| 3-one | C=O | | | | 161.6 |
| | C4 | | | | 111.5 |
| | C5 | | | | 147.4 |
| 5-methyl | CH3 | 2.31 | 6 | | 14.3 |
| Both ends of cross-linking part (L) | CH | 7.40 | 2 | d 13.4 Hz | 146.3 |
| Center of cross-linking part (L) | CH | 7.74 | 1 | t 13.4 Hz | 117.4 |
| | OH | 9.21 | 1.4 | | |

Figure 8A:
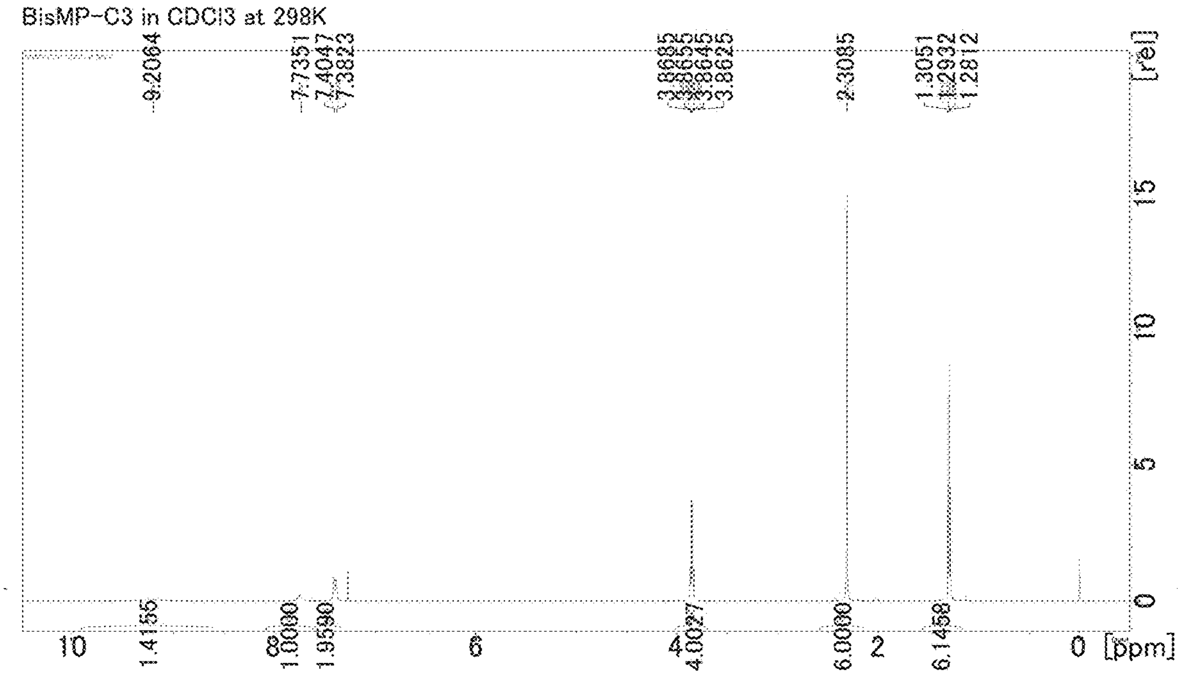
FIG. 8 shows graphs showing the $^1$H-NMR spectrum in Example 8.
Figure 8B:
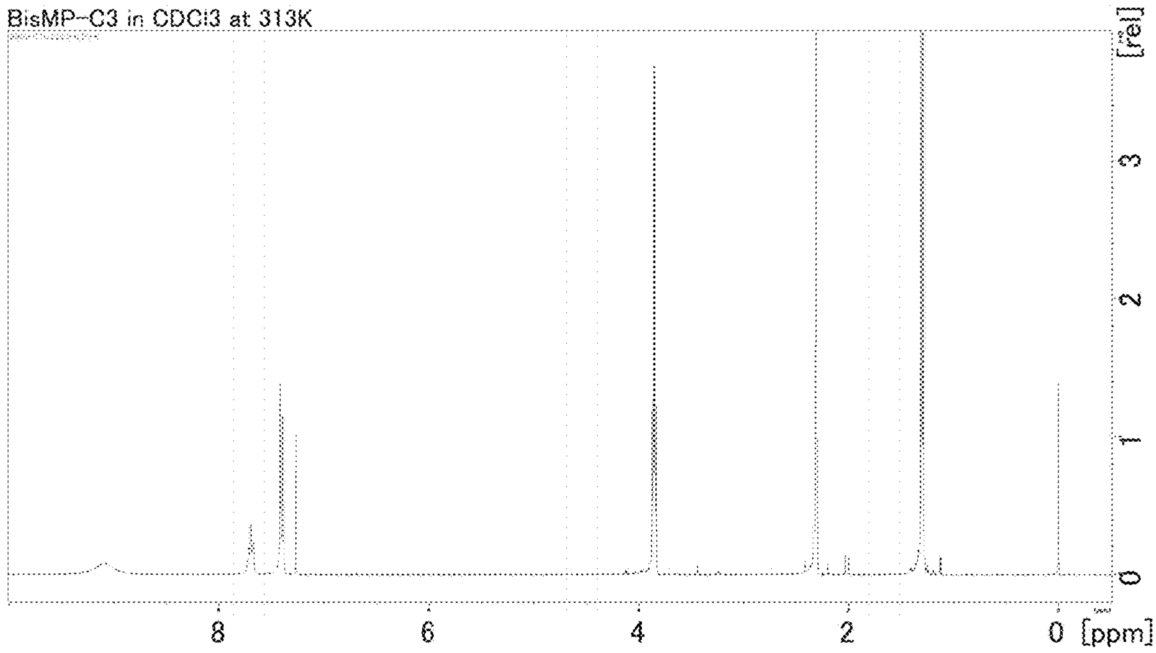
Figure 9:
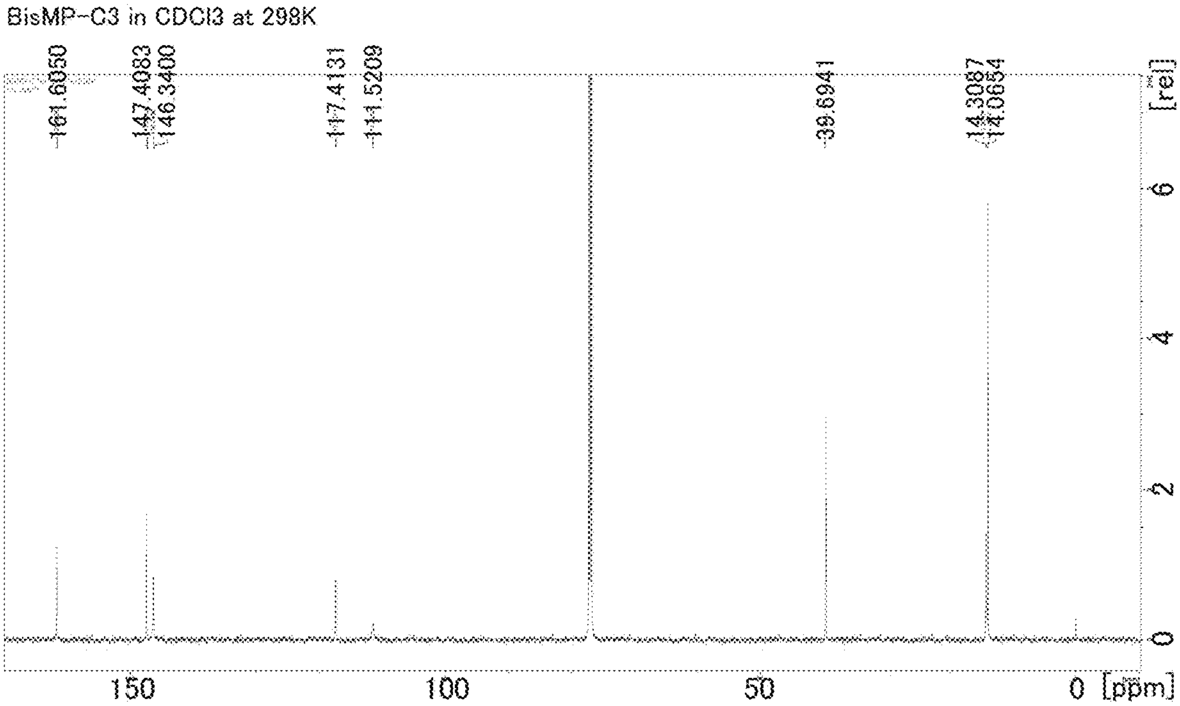
FIG. 9 is a graph showing the $^{13}$C-NMR spectrum in Example 8.

FIG. 8 shows graphs showing the $^1$H-NMR spectrum; FIG. 9 is a graph showing the $^{13}$C-NMR spectrum. In FIG. 8, (A) shows the result of 298 K, and (B) shows the result of 313 K. In FIGS. 8 and 9, the horizontal axis indicates the chemical shift value, and the vertical axis indicates the relative intensity. As shown in FIG. 8, three signals (7.73, 7.40, and 7.38) of the benzene ring and signals of three protons bonded to the conjugated double bond of the cross-linking part have been observed to be broad by chemical exchange by keto-enol rearrangement, and it was found that the linker region (L) forms a conjugated system. Also, of the three protons, one proton in the center was observed at 7.74 ppm at the lowest magnetic field, and two protons close to edaravone at both ends were observed at 7.40 ppm, and the effect also appears on the methyl group, resulting in a signal (2.31 ppm). These showed that an isomer of cis-cis, cis-trans, trans-cis, or trans-trans was formed by the two double bonds of L. These results showed that, since the keto-enol isomerism occurs and the position of the double bond moves between neighboring atoms in the hydroxy group of $R^3$, BisEp-C3 forms a tautomer of the following formula E and a geometric isomer (cis-trans isomer) of these.

[formula E]

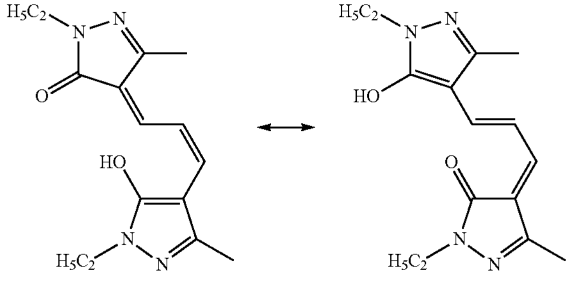

Tautomer

These results showed that the compound contained in the antioxidant of the present invention forms a conjugated system and has a tautomer. The results also suggested that a similar conjugated system establishes when L is an alkenyl group having an even number of carbon atoms.

Example 9

It was examined that the antioxidant of the present invention scavenges reactive oxygen species in vivo.

Oxidative stress caused by reactive oxygen species is known to reduce NO production in vascular endothelial cells, resulting in vasoconstriction and decreased blood flow. Therefore, using vasodilation as an indicator, it was examined whether the antioxidant of the present invention scavenges reactive oxygen species in vivo.

Eight-week old or older female rats (Wistar, body weight: approximately 200 g, n=1) were anesthetized by subcutaneous administration of urethane so as to be 7 g/kg body weight. The hair of the auricles of the rats was then removed and the rats were fixed on a fixing table. After the fixing, the fixing table was placed under a microscope (Nikon OPTIphoto, produced by Nikon Corporation). In addition, a catheter was placed in the groin vein of the rat.

BisEP-C3 was dissolved in a saline solution to achieve a concentration of 3 mg/ml. The resulting saline solution containing BisEP-C3 was administered intravenously via the catheter so as to be 3 mg/kg body weight. Then, the hemodynamic course of the rat auricular subcutaneous blood vessel was photographed and recorded using a microscope at a predetermined period of time (30, 60, 120 or 180 minutes) before and after the administration.

The obtained images were classified into three blood vessel thicknesses (thick: 35-45 μm, medium: 15-20 μm, thin: 7-9 μm) based on the diameter of the blood vessel before administration. Next, in the vein in the obtained image, a plurality of sites where there was no branch of the blood vessel and the blood vessel was in focus were selected for each classification of the blood vessel. Further, for each selected site, the relative blood vessel diameter was calculated after the measurement of the blood vessel diameter, with the blood vessel diameter before administration being a reference (1). Then, the average value of the relative blood vessel diameters was obtained for each classification of the blood vessel diameters. As a control, the blood vessel diameter was calculated in the same manner except that the saline solution was administered. The results are shown in FIG. 10.

Figure 10A:
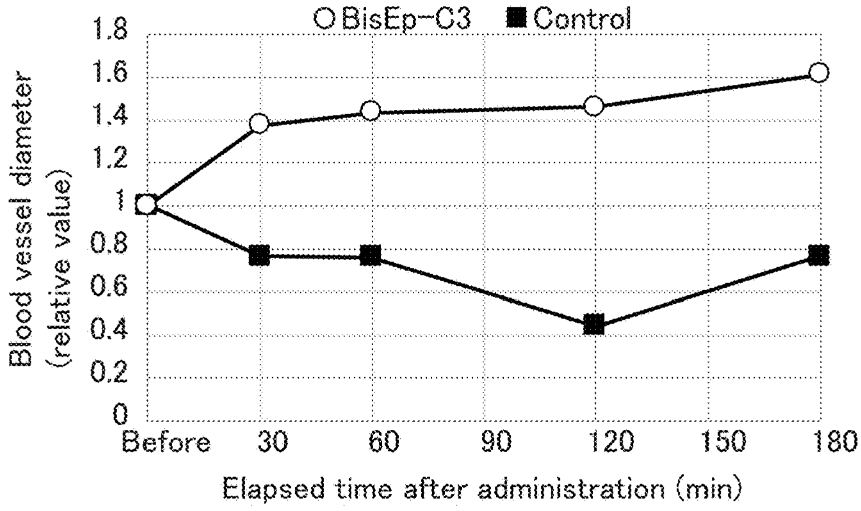
FIG. 10 shows graphs showing change of the blood vessel diameter after administration of the antioxidant of the present invention in Example 9.
Figure 10B:
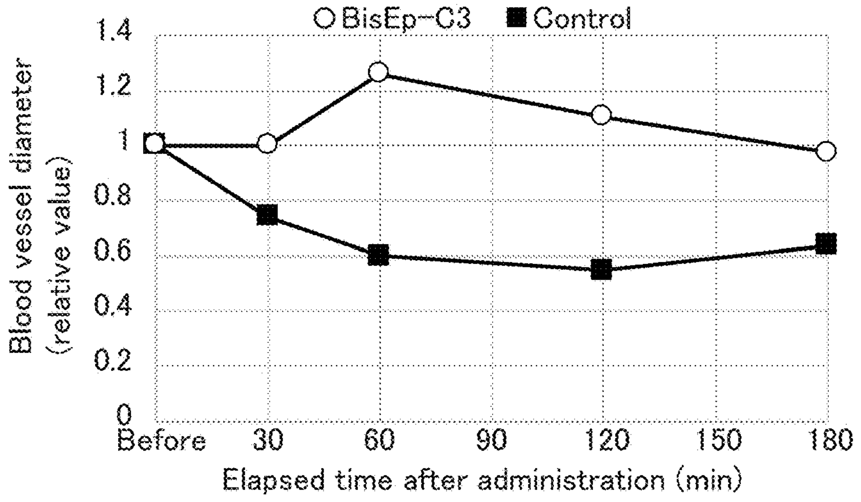
Figure 10C:
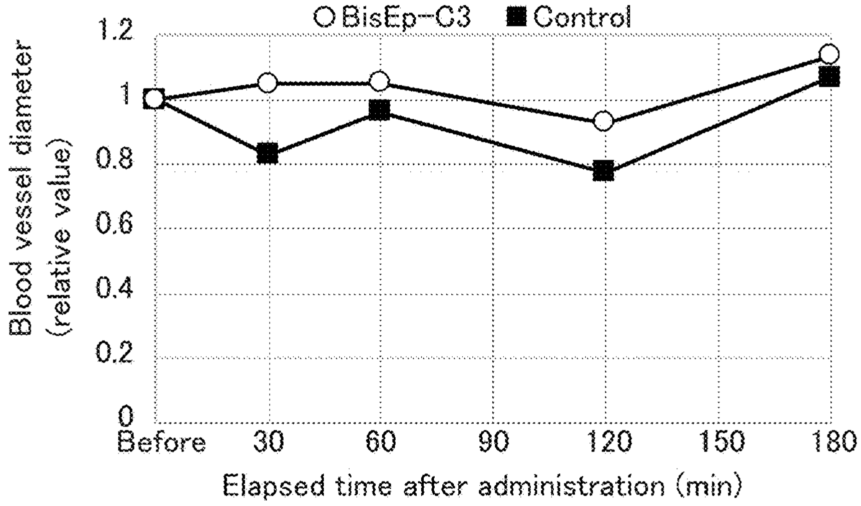
Figure 11A:
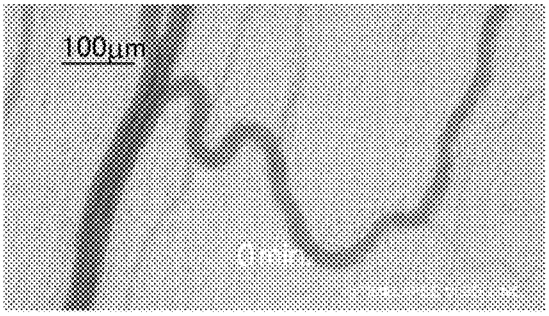
FIG. 11 shows photographs showing the results of the mesentery of the control in Example 10.
Figure 11B:
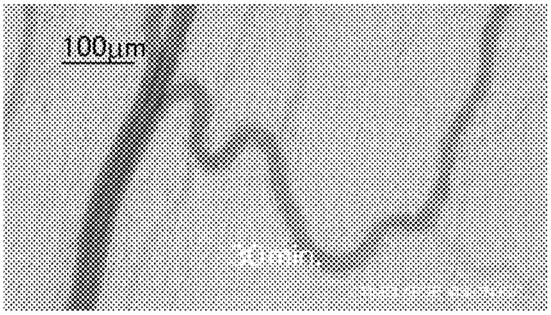
Figure 11C:
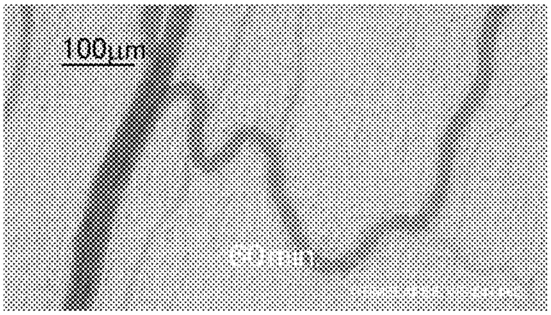
Figure 11D:
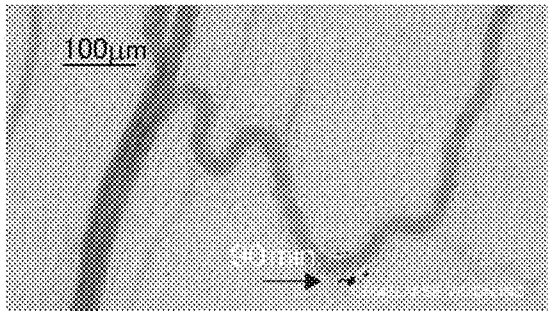
Figure 11E:
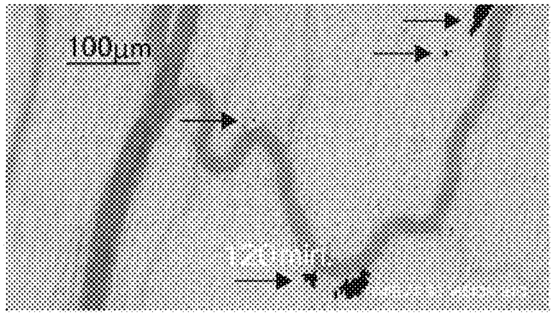
Figure 11F:
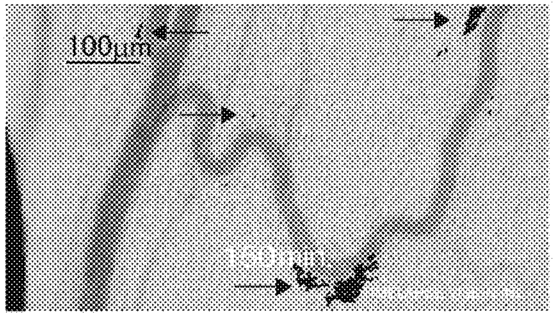
Figure 11G:
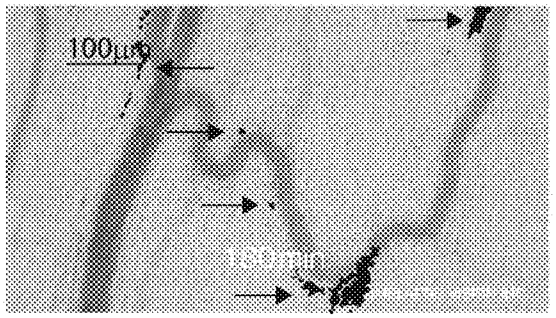
Figure 12A:
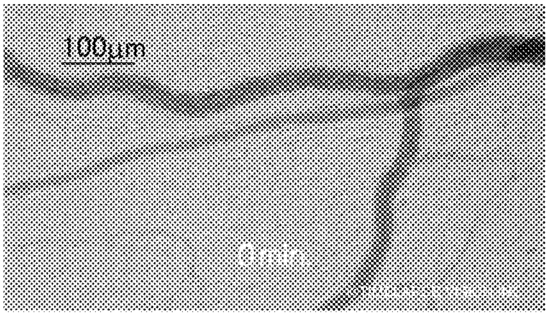
FIG. 12 shows photographs showing the results of the mesentery of rats administered with BisEP-C3 in Example 10.
Figure 12E:
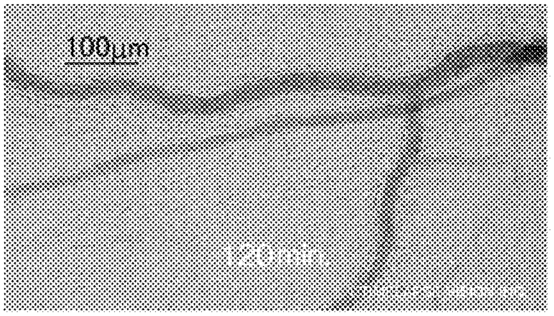
Figure 12B:
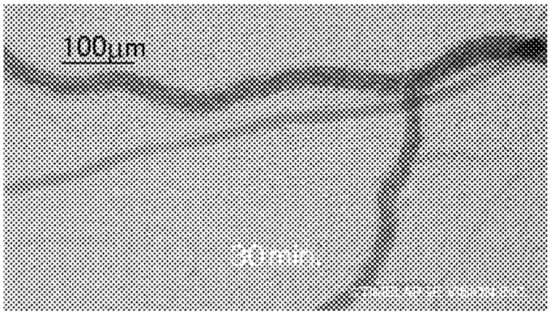
Figure 12F:
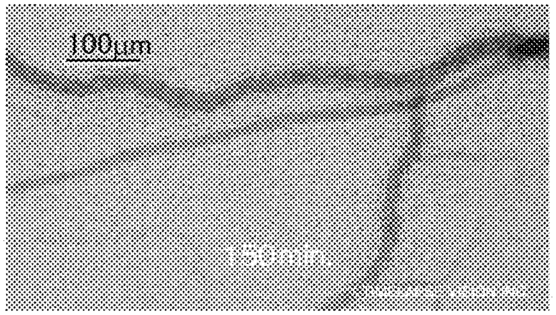
Figure 12C:
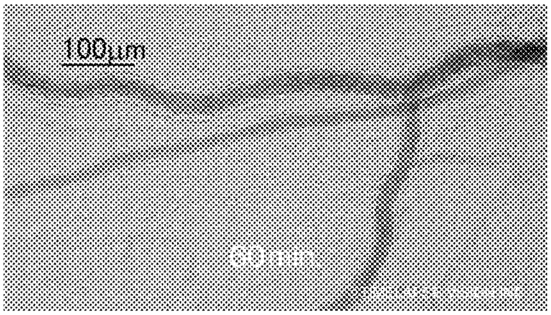
Figure 12G:
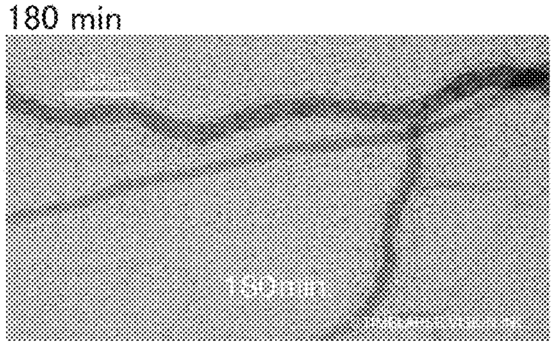
Figure 12D:
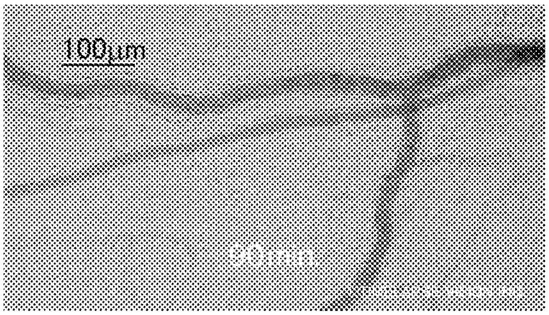

FIG. 10 shows graphs showing the change of blood vessel diameter after administration of the antioxidant of the present invention, (A) shows the result of a thin blood vessel, (B) shows the result of a medium blood vessel, and (C) shows the result of a thick blood vessel. In FIG. 10A to 10C, the horizontal axis indicates the elapsed time after administration, and the vertical axis indicates the relative value of the blood vessel diameter. As shown in FIG. 10 A to 10C, when BisEp-C3 was administered, the blood vessel diameter was dilated at any time after administration as compared to the control. Further, while the blood vessel diameter was dilated regardless of the size of the blood vessel when BisEp-C3 was administered, the severity of dilatation of the blood vessel diameter was remarkably observed in the smaller blood vessels. These results showed that the antioxidant of the present invention can induce vasodilation in vivo. Also, as described above, oxidative stress caused by reactive oxygen species reduces NO production in vascular endothelial cells, resulting in vasoconstriction and decreased blood flow. Since the antioxidant of the present invention can eliminate reactive oxygen species and induce vasodilation in vivo, it was found that the antioxidant of the present invention eliminates reactive oxygen species and reduces oxidative stress, thereby enhancing NO production in vascular endothelial cells, resulting in vasodilation.

Example 10

It was examined that the antioxidant of the present invention scavenges reactive oxygen species in vivo.

Administration of lipopolysaccharide to the mesentery vicinity blood vessels generates reactive oxygen species (ROS), causing vascular disorder and bleeding. Therefore, using the bleeding area as an indicator, it was examined whether the antioxidant of the present invention scavenges ROS in vivo.

Eight-week old or older female rats (Wistar, body weight: approximately 200 g, n=1) were anesthetized by subcutaneous administration of urethane (1.75 g/kg body weight). The rats were then opened and fixed on a fixing table in such a manner that the mesentery of the rats was observable. After the fixing, the fixing table was placed under a microscope (Nikon OPTIphoto, produced by Nikon Corporation) so that the mesentery could be observed. In addition, a catheter was placed in the groin vein of the rat.

1 μg/ml of lipopolysaccharide ((LPS), produced by Sigma-Aldrich Co., Ltd.) derived from *Pseudomonas aeruginosa* (ATCC27316) was added dropwise once (20 μL, 20 ng/sight) and allowed to stand for 30 minutes. Next, a saline solution containing BisEP-C3 prepared in the same manner as in Example 9 was rapidly administered intravenously via the catheter so as to be 1 mg/kg body weight. After the intravenous administration, the saline solution was administered continuously so as to be 1 mg/kg body weight per hour (0.15 ml/hour). In addition, in parallel with the administration of the saline solution containing LPS and BisEP-C3, one visual field, including the blood vessel of the mesentery, was photographed over time. In the obtained photograph, the area of the region where bleeding occurred (bleeding area) was detected based on the number of pixels, and then the proportion of the area (bleeding area proportion) occupied per visual field was calculated. As a control, the experiment was performed in the same manner except that a saline solution was administered instead of the saline solution containing BisEP-C3. The results are shown in FIG. 11.

FIG. 11 shows photographs showing the results of the mesentery of the control, and (A) to (G) are photographs at the time of LPS instillation (0 minutes) and 30, 60, 90, 120, 150, and 180 minutes after LPS instillation, respectively. In FIG. 11, a black region indicated by an arrow is a region in which bleeding has occurred.

FIG. 12 shows photographs showing the results of the mesentery of rats administered with BisEP-C3, and (A) to (G) are photographs at the time of LPS instillation (0 minutes) and at 30, 60, 90, 120, 150, and 180 minutes after LPS instillation, respectively.

Figure 13A:
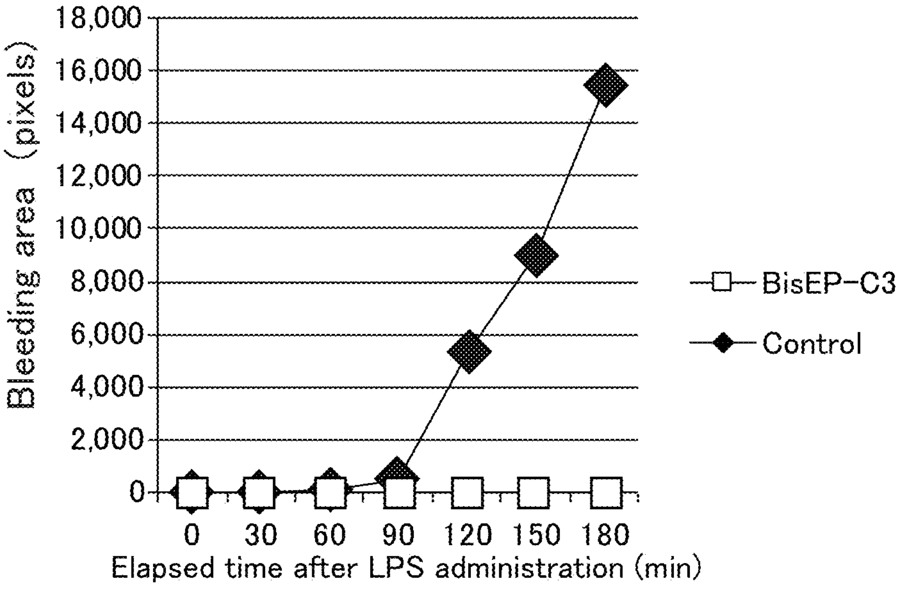
FIG. 13 shows graphs showing the bleeding area and the bleeding area proportion in Example 10.
Figure 13B:
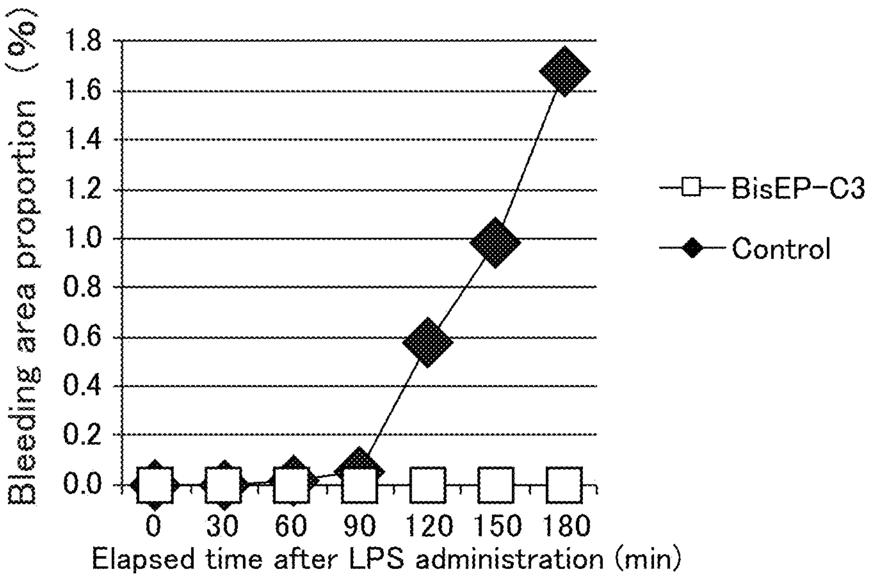

FIG. 13 shows graphs showing the bleeding area and the bleeding area proportion. In FIG. 13, (A) shows the result of the bleeding area, and (B) shows the result of the bleeding area proportion. In (A) in FIG. 13, the horizontal axis indicates elapsed time after LPS administration, and the vertical axis indicates the bleeding area. In (B) in FIG. 13, the horizontal axis indicates elapsed time after LPS administration, and the vertical axis indicates the bleeding area proportion. As shown in FIGS. 11 and 13, in the control, bleeding to the periphery was observed in the mesenteric blood vessel from 90 minutes after LPS administration, and the region of bleeding increased with time. In contrast, as shown in FIGS. 12 and 13, in the BisEP-C3 administration group, no bleeding was observed after the LPS administration. Administration of LPS generates reactive oxygen species in the organism and causes vascular disorders. Therefore, it was presumed that the protective agent of the present invention prevents vascular disorders by scavenging the reactive oxygen species in vivo.

In addition, the rolling phenomena of leukocytes in the blood of rats administered with BisEP-C3 and controls were examined over time after LPS instillation. In the control, no rolling phenomenon of leukocytes was observed in the blood vessel after LPS instillation. This is thought to be because the instillation of LPS increases the NO production by inducible NO synthase and also increases the production of ROS from neutrophils, so that NO reacts with superoxide in ROS to form peroxynitrite with high oxidizing power, exhibits cytotoxicity, and causes vascular disorders. In contrast, a large number of rolling phenomena of leukocytes were observed in rats administered with BisEP-C3 as compared to the control. This is thought to be because, although the instillation of LPS increases the NO production by inducible NO synthase and also increases the production of ROS from neutrophils, BisEP-C3 scavenges ROS and reduces the peroxynitrite production, thereby suppressing the cytotoxicity.

These results showed that the antioxidant of the present invention scavenges reactive oxygen species in vivo.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2019-011929, filed on Jan. 28, 2019. The entire subject matter of the Japanese Patent Applications is incorporated herein by reference.

Supplementary Notes

Some or all of the above embodiments and examples may be described as in the following Supplementary Notes, but are not limited thereto.

Supplementary Note 1

An antioxidant including:

a compound represented by the following formula (1) or a salt thereof:

(1)

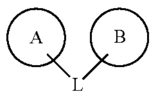

where in the formula (1), an A ring and a B ring may be the same or different and are a pyrazole ring having a substituent or a pyrazoline ring having a substituent, and L is a saturated or unsaturated hydrocarbon group.

Supplementary Note 2

The antioxidant according to Supplementary Note 1, wherein the A ring and the B ring may be the same or different and are represented by the following formula (2) or (3):

(2)

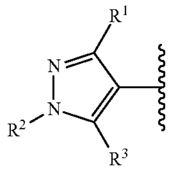

(3)

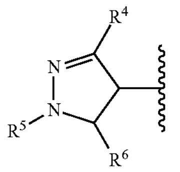

where in the formula (2), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and where in the formula (3), $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent.

Supplementary Note 3

The antioxidant according to Supplementary Note 1 or 2, wherein

L is an unsaturated hydrocarbon group having 1 to 6 carbon atoms.

Supplementary Note 4

The antioxidant according to any one of Supplementary Notes 1 to 3, wherein the compound represented by the formula (1) includes a compound represented by the following formula (4):

(4)

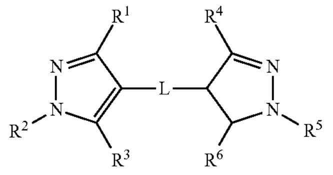

where in the formula (4), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^4$ is a hydrogen atom, a halogen atom, or an alkyl group, $R^5$ is an alkyl group or an aryl group that may have a substituent, $R^6$ is a hydrogen atom, an oxygen atom, a halogen atom, or a hydroxy group, and L is a saturated or unsaturated hydrocarbon group having 1 to 6 carbon atoms.

Supplementary Note 5

The antioxidant according to any one of Supplementary Notes 1 to 4, wherein the compound represented by the formula (1) includes a compound represented by the following formula (5):

(5)

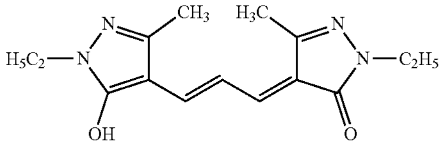

Supplementary Note 6

The antioxidant according to any one of Supplementary Notes 1 to 4, wherein the compound represented by the formula (1) includes a compound represented by the following formula (6):

(6)

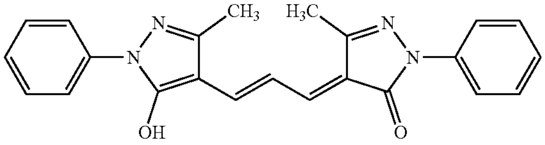

Supplementary Note 7

The antioxidant according to any one of Supplementary Notes 1 to 3, wherein the compound represented by the formula (1) includes a compound represented by the following formula (12):

(12)

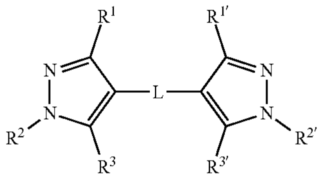

where in the formula (12), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^{1'}$ is a hydrogen atom, a halogen atom, or an alkyl group, $R^{2'}$ is an alkyl group or an aryl group that may have a substituent, $R^{3'}$ is a hydrogen atom, a halogen atom, an alkyl group, or a hydroxy group, and L is a saturated or unsaturated hydrocarbon group having 1 to 6 carbon atoms.

Supplementary Note 8

The antioxidant according to any one of Supplementary Notes 1, 2, and 7, wherein the compound represented by the formula (1) includes a compound represented by the following formula (13):

(13)

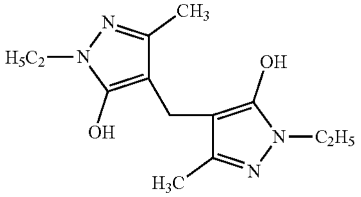

Supplementary Note 9

A cytoprotective agent including:

the antioxidant according to any one of Supplementary Notes 1 to 8.

Supplementary Note 10

A pharmaceutical for a disease caused by oxidative stress, including:

the antioxidant according to any one of Supplementary Notes 1 to 8.

Supplementary Note 11

The pharmaceutical according to Supplementary Note 10, wherein the oxidative stress is stress caused by reactive oxygen species.

Supplementary Note 12

The pharmaceutical according to Supplementary Note 10 or 11, wherein the disease caused by oxidative stress is cerebral infarction, amyotrophic lateral sclerosis, Alzheimer's disease, or Parkinson's disease.

Supplementary Note 13

An antioxidation method using the antioxidant according to any one of Supplementary Notes 1 to 8.

Supplementary Note 14

The antioxidation method according to Supplementary Note 13, including the step of:

contacting with the antioxidant.

Supplementary Note 15

The antioxidation method according to Supplementary Note 14, wherein the antioxidant is contacted in vitro or in vivo.

Supplementary Note 16

A cell protection method using the cytoprotective agent according to Supplementary Note 9.

Supplementary Note 17

The cell protection method according to Supplementary Note 16, including the step of:

causing cells to coexist with the cytoprotective agent.

Supplementary Note 18

A method for treating a disease caused by oxidative stress, including the step of:

administering to a patient the pharmaceutical according to any one of Supplementary Notes 10 to 12.

Supplementary Note 19

The method according to Supplementary Note 18, wherein the oxidative stress is stress caused by reactive oxygen species.

Supplementary Note 20

The method according to Supplementary Note 18 or 19, wherein the disease caused by oxidative stress is cerebral infarction, amyotrophic lateral sclerosis, Alzheimer's disease, or Parkinson's disease.

Supplementary Note 21

A pyrazole ring derivative or a salt thereof represented by the following formula (4):

(4)

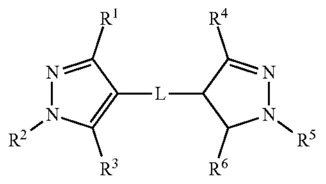

where in the formula (4), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is an alkyl group having 2 or more carbon atoms, $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is an alkyl group having 2 or more carbon atoms, $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, L is a saturated or unsaturated hydrocarbon group.

Supplementary Note 22

Use of a compound represented by the following formula (1) or a salt thereof for use in antioxidation:

(1)

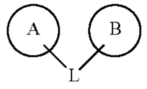

where in the formula (1), an A ring and a B ring may be the same or different and are a pyrazole ring having a substituent or a pyrazoline ring having a substituent, and L is a saturated or unsaturated hydrocarbon group.

Supplementary Note 23

Use of a compound represented by the following formula (1) or a salt thereof for use in cell protection:

(1)

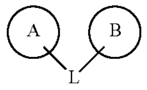

where in the formula (1), an A ring and a B ring may be the same or different and are a pyrazole ring having a substituent or a pyrazoline ring having a substituent, and L is a saturated or unsaturated hydrocarbon group.

Supplementary Note 24

Use of a compound represented by the following formula (1) or a salt thereof for use in treatment of a disease caused by oxidative stress:

(1)

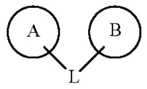

where in the formula (1), an A ring and a B ring may be the same or different and are a pyrazole ring having a substituent or a pyrazoline ring having a substituent, and L is a saturated or unsaturated hydrocarbon group.

INDUSTRIAL APPLICABILITY

As described above, according to the present invention, by including the compound represented by the formula (1) or a salt thereof, reactive oxygen species can be scavenged. Thus, the antioxidant of the present invention can be used, for example, as a protective agent against the cytotoxicity of the reactive oxygen species in vivo, and can be used, for example, as a pharmaceutical for a disease caused by oxidative stress. Therefore, the present invention is extremely useful, for example, in the field of pharmaceuticals and the like.

The invention claimed is:

1. A compound represented by the following formula (1) or a salt thereof:

(1)

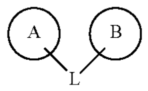

where in the formula (1), an A ring and a B ring may be the same or different and represented by the following formula (2) or (3):

(2)

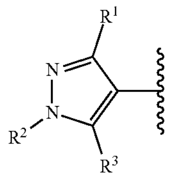

(3)

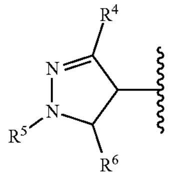

where in the formula (2), $R^1$ is a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is a halogen atom, an alkyl group, an amino group, a cyano group, a hydroxy group, a sulfo group, a carboxyl group, an alkoxy group, a hydroxyalkyl group, an acyl group, or an alkynyl group that may have a substituent, and $R^3$ is a halogen atom, an amino group, a cyano group, a hydroxy group, a sulfo group, a carboxyl group, an alkoxy group, a hydroxyalkyl group, an acyl group, an alkynyl group, or an aryl group that may have a substituent, and where in the formula (3), $R^4$ is a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and $R^6$ is an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and L is a saturated hydrocarbon group having 2 to 6 carbon atoms.

2. The compound antioxidant according to claim 1, wherein the compound represented by the formula (1) is a compound represented by the following formula (4):

(4)

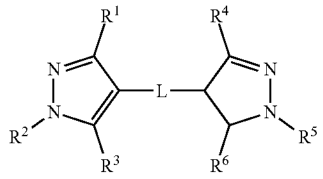

where in the formula (4), $R^1$ is a halogen atom, or an alkyl group, $R^2$ is an alkyl group or an aryl group that may have a substituent, $R^3$ is a halogen atom, or a hydroxy group, $R^4$ is a halogen atom, or an alkyl group, $R^5$ is an alkyl group or an aryl group that may have a substituent, $R^6$ is an oxygen atom, a halogen atom, or a hydroxy group, and L is a saturated hydrocarbon group having 2 to 6 carbon atoms.

3. The compound according to claim 1, wherein the compound represented by the formula (1) is a compound represented by the following formula (12):

(12)

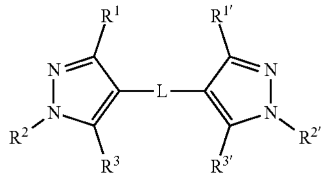

where in the formula (12), $R^1$ is a halogen atom or an alkyl group, $R^2$ is an alkyl group that may have a substituent, $R^3$ is a halogen atom or a hydroxy group, $R^{1'}$ is a halogen atom or an alkyl group, $R^{2'}$ is an alkyl group that may have a substituent, $R^{3'}$ is a halogen atom, an alkyl group, or a hydroxy group, and L is a saturated hydrocarbon group having 2 to 6 carbon atoms.

4. A cell protection or antioxidation method comprising contacting a cell with the compound according to claim 1.

5. An antioxidation method comprising:

administering the compound of claim 1 to a subject having oxidative stress caused by reactive oxygen species.

6. The antioxidation method according to claim 4, wherein the contacting is in vitro.

7. A method for treating a disease caused by oxidative stress caused by reactive oxygen species, comprising the step of:

administering to a patient the compound according to claim 1.

8. The method according to claim 7, wherein the disease caused by oxidative stress is cerebral infarction, amyotrophic lateral sclerosis, Alzheimer's disease, or Parkinson's disease.

9. A compound represented by the following formula (13) or a salt thereof:

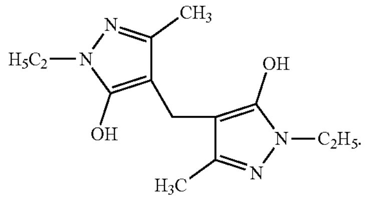

(13)

10. The antioxidation method according to claim 4, wherein the contacting is in vivo.

11. A cell protection or antioxidation method comprising contacting a cell with the compound according to claim 9.

12. An antioxidation method comprising:

administering the compound of claim 9 to a subject having oxidative stress caused by reactive oxygen species.

13. The antioxidation method according to claim 11, wherein the contacting is in vitro.

14. The antioxidation method according to claim 11, wherein the contacting is in vivo.

15. A method for treating a disease caused by oxidative stress caused by reactive oxygen species in a subject in need thereof, comprising administering to the subject the compound according to claim 9.

16. The method according to claim 15, wherein the subject is human.

17. The method according to claim 15, wherein the disease caused by oxidative stress is cerebral infarction, amyotrophic lateral sclerosis, Alzheimer's disease, or Parkinson's disease.

* * * * *